(12) United States Patent
Fujiwara

(10) Patent No.: US 10,517,473 B2
(45) Date of Patent: Dec. 31, 2019

(54) ENDOSCOPE LIGHT SOURCE APPARATUS

(71) Applicant: OLYMPUS CORPORATION, Hachioji-shi, Tokyo (JP)

(72) Inventor: Kazuto Fujiwara, Saitama (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/168,606

(22) Filed: Oct. 23, 2018

(65) Prior Publication Data

US 2019/0059712 A1 Feb. 28, 2019

Related U.S. Application Data

(63) Continuation of application No. PCT/JP2017/012116, filed on Mar. 24, 2017.

(30) Foreign Application Priority Data

Sep. 16, 2016 (JP) .................................. 2016-181116

(51) Int. Cl.
*A61B 1/07* (2006.01)
*G02B 23/26* (2006.01)
(Continued)

(52) U.S. Cl.
CPC ............ *A61B 1/07* (2013.01); *A61B 1/00071* (2013.01); *A61B 1/0638* (2013.01); *A61B 1/0684* (2013.01); *G02B 23/26* (2013.01)

(58) Field of Classification Search
CPC . A61B 1/00071; A61B 1/00105; A61B 1/042; A61B 1/043; A61B 1/0638; A61B 1/0646; A61B 1/0684; G02B 23/26
See application file for complete search history.

(56) References Cited

U.S. PATENT DOCUMENTS 8,810,126 B2 * 8/2014 Ito ....................... A61B 1/0638
313/503
2003/0229270 A1 12/2003 Suzuki et al.
(Continued)

FOREIGN PATENT DOCUMENTS

EP 2679137 A1 1/2014
JP 4054222 B2 2/2008
(Continued)

OTHER PUBLICATIONS

International Search Report (ISR) dated Jun. 13, 2017 issued in International Application No. PCT/JP2017/012116.
(Continued)

*Primary Examiner* — Anabel Ton
(74) *Attorney, Agent, or Firm* — Holtz, Holtz & Volek PC

(57) ABSTRACT

Provided is an endoscope light source apparatus including: first and second solid-state light sources that emit first and second light beams, respectively; a third solid-state light source that emits a third light beam that generates white light by being combined with the first and second light beams; an optical member that combines the first, second, and third light beams to generate a combined light; an optical filter that is provided so as to be insertable into/retractable from an optical path of the combined light; and a controller, wherein, in a first excitation-light illumination mode, the controller turns on the first and second solid-state light sources and weakly turns on the third solid-state light source, and, in a second excitation-light illumination mode, turns on the first solid-state light source, turns off the second solid-state light source, and weakly turns on the third solid-state light source.

7 Claims, 24 Drawing Sheets

(51) Int. Cl.
  *A61B 1/00* (2006.01)
  *A61B 1/06* (2006.01)

(56) References Cited

U.S. PATENT DOCUMENTS

2013/0096376 A1    4/2013   Takei et al.
2016/0270642 A1*   9/2016   Morita .................... A61B 1/04

FOREIGN PATENT DOCUMENTS

| | | |
|---|---|---|
| JP | 2011194040 A | 10/2011 |
| JP | 2014161639 A | 9/2014 |
| JP | 2015130910 A | 7/2015 |
| JP | 2016123576 A | 7/2016 |
| WO | 2012169270 A1 | 12/2012 |

OTHER PUBLICATIONS

Written Opinion dated Jun. 13, 2017 issued in International Application No. PCT/JP2017/012116.

* cited by examiner

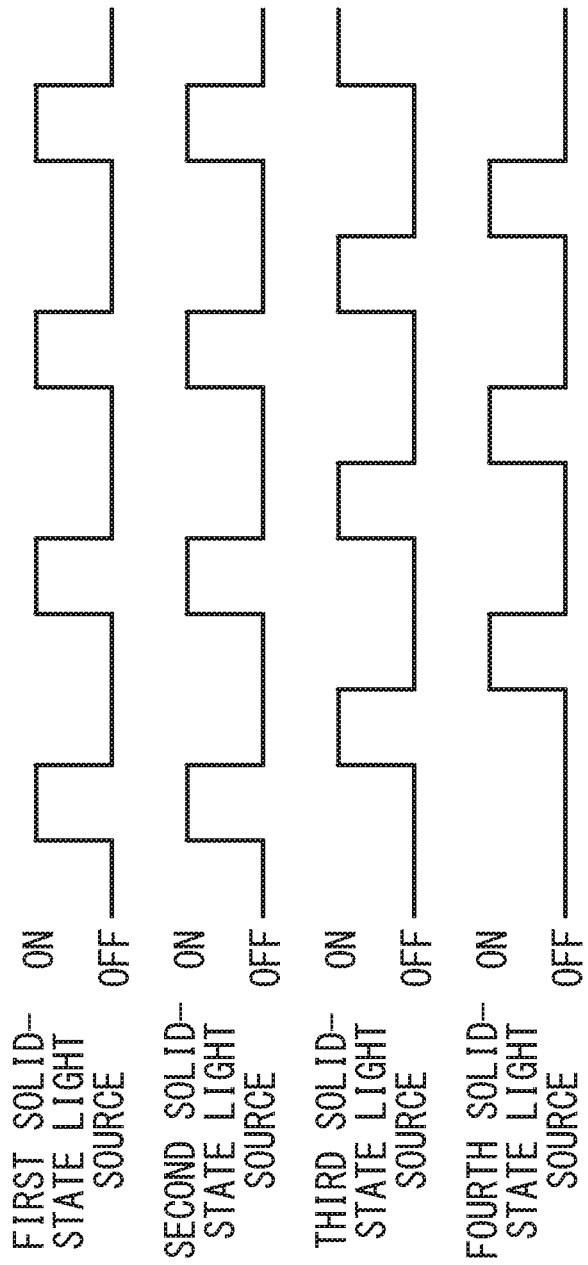

WHITE LIGHT

BINOCULAR TYPE

MONOCULAR TYPE

ENDOSCOPE LIGHT SOURCE APPARATUS

CROSS-REFERENCE TO RELATED APPLICATIONS

This is a continuation of International Application PCT/JP2017/012116, with an international filing date of Mar. 24, 2017, which is hereby incorporated by reference herein in its entirety. This application claims the benefit of Japanese Patent Application No. 2016-181116, filed on Sep. 16, 2016, the content of which is incorporated herein by reference.

TECHNICAL FIELD

The present invention relates to an endoscope light source apparatus, and relates, in particular, to an endoscope light source apparatus having two types of illumination modes for performing fluorescence observation.

BACKGROUND ART

In the related art, fluorescence endoscopes with which fluorescence coming from a living organism is observed by radiating excitation light thereon have been employed for the purpose of early detection of cancer or the like (for example, see Patent Literature 1). The fluorescence endoscopes include: binocular types provided with a white-light-observation-dedicated image-acquisition device and a fluorescence-observation-dedicated image-acquisition device; and monocular types provided with a single image-acquisition device that serves for performing both white-light observation and fluorescence observation. An endoscope light source apparatus described in Patent Literature 1 realizes illumination modes that are suitable for a binocular-type fluorescence endoscope and a monocular-type fluorescence endoscope, respectively, by using a single lamp light source and by changing combinations of a plurality of filters to be disposed on an optical path.

CITATION LIST

Patent Literature

{PTL 1} Publication of Japanese Patent No. 4054222

SUMMARY OF INVENTION

Technical Problem

An object of the present invention is to provide an endoscope light source apparatus with which it is possible to realize, by employing a compact configuration, two types of illumination modes for performing fluorescence observation.

Solution to Problem

An aspect of the present invention is an endoscope light source apparatus including: a first solid-state light source that is configured to emit a first light beam that includes a first wavelength band; a second solid-state light source that is configured to emit a second light beam that includes a second wavelength band in which a wavelength thereof is longer than in the first wavelength band; a third solid-state light source that is configured to emit a third light beam that includes a third wavelength band differing from the first and second wavelength bands and that generates white light by being combined with at least of the first and second light beams; an optical member that is configured to combine the first light beam and the second light beam with the third light beam to generate a combined light; an optical member that is configured to combine the first light beam and the second light beam with the third light beam to generate a combined light; an optical filter that is configured to be provided so as to be insertable into/retractable from an optical path of the combined light, and that selectively allows the light in the first, second, and third wavelength bands to pass therethrough; and a controller that is configured to control turning on/off of the first, second, and third solid-state light sources, and insertion/retraction of the optical filter, wherein in a white-light illumination mode, the controller causes the optical filter to be retracted from the optical path, and turns on the first, second, and third solid-state light sources, in a first excitation-light illumination mode, the controller causes the optical filter to be inserted into the optical path, turns on the first and second solid-state light sources, and turns on the third solid-state light source so that an intensity of the third light beam becomes lower than intensities of the first light beam and the second light beam, and, in a second excitation-light illumination mode, the controller causes the optical filter to be inserted into the optical path, turns on the first solid-state light source, turns off the second solid-state light source, and turns on the third solid-state light source so that the intensity of the third light beam becomes lower than the intensity of the first light beam.

In the above-described aspect, the optical member may include a first optical member that is configured to combine the first light beam and the second light beam, and a second optical member that is configured to combine the combined light of the first and second light beams generated by the first optical member with the third light beam.

In the above-described aspect, the first wavelength band may be from 390 nm to 440 nm, and the second wavelength band may be from 440 nm to 470 nm.

In the above-described aspect, the first optical member may have a first dichroic mirror surface that allows one of the first light beam and the second light beam to pass therethrough and reflects the other, the first dichroic mirror surface may possess a first cut-off wavelength at which a transmittance on a transmission-optical-path side thereof becomes 50% and the first light beam and the second light beam overlap with each other, and an intensity of the combined light of the first and second light beams at the first cut-off wavelength may be equal to or greater than 10% of a maximum intensity thereof.

In the above-described aspect, the second optical member may have a second dichroic mirror surface that allows one of the combined light of the first and second light beams and the third light beam to pass therethrough and reflects the other, the second dichroic mirror surface may possess a second cut-off wavelength at which a transmittance on a transmission-optical-path side thereof becomes 50% and the combined light of the first and second light beams and the third light beam overlap with each other, and an intensity of the combined light of the first, second, and third light beams at the second cut-off wavelength may be equal to or greater than 10% of a maximum intensity thereof.

In the above-described aspect, the first optical member may have a first dichroic mirror surface that allows light in the first wavelength band to pass therethrough and reflects light in the second wavelength band, and the first light beam and the first dichroic mirror surface may possess optical characteristics that satisfy conditional expression (1) below, where I1max is the maximum intensity of the first light beam in the first wavelength band, I1 is the intensity of the first light beam at a wavelength 10 nm or more away from the first wavelength band on a long-wavelength side thereof, and T1 is the transmittance (%) of the first dichroic mirror surface at a wavelength 10 nm or more away from the first wavelength band on a long-wavelength side thereof.

$$(I1/I1\ max) \times T1 \leq 0.01 \qquad (1)$$

In the above-described aspect, the second light beam and the optical filter may possess optical characteristics that satisfy conditional expression (2) below, where I2 max is the maximum intensity of the second light beam in the second wavelength band, I2 is the intensity of the second light beam at a wavelength 10 nm or more away from the second wavelength band on a long-wavelength side thereof, and T2 is the transmittance (%) of the optical filter at a wavelength 10 nm or more away from the second wavelength band on a long-wavelength side thereof.

$$(I2/I2\ max) \times T2 \leq 0.01 \qquad (2)$$

BRIEF DESCRIPTION OF DRAWINGS

FIG. 19A is a diagram showing a timing chart indicating the operations of the first, second, third, and fourth solid-state light sources in the white-light illumination mode.

DESCRIPTION OF EMBODIMENT

An endoscope light source apparatus 1 according to an embodiment of the present invention will be described below with reference to the drawings.

Figure 1:
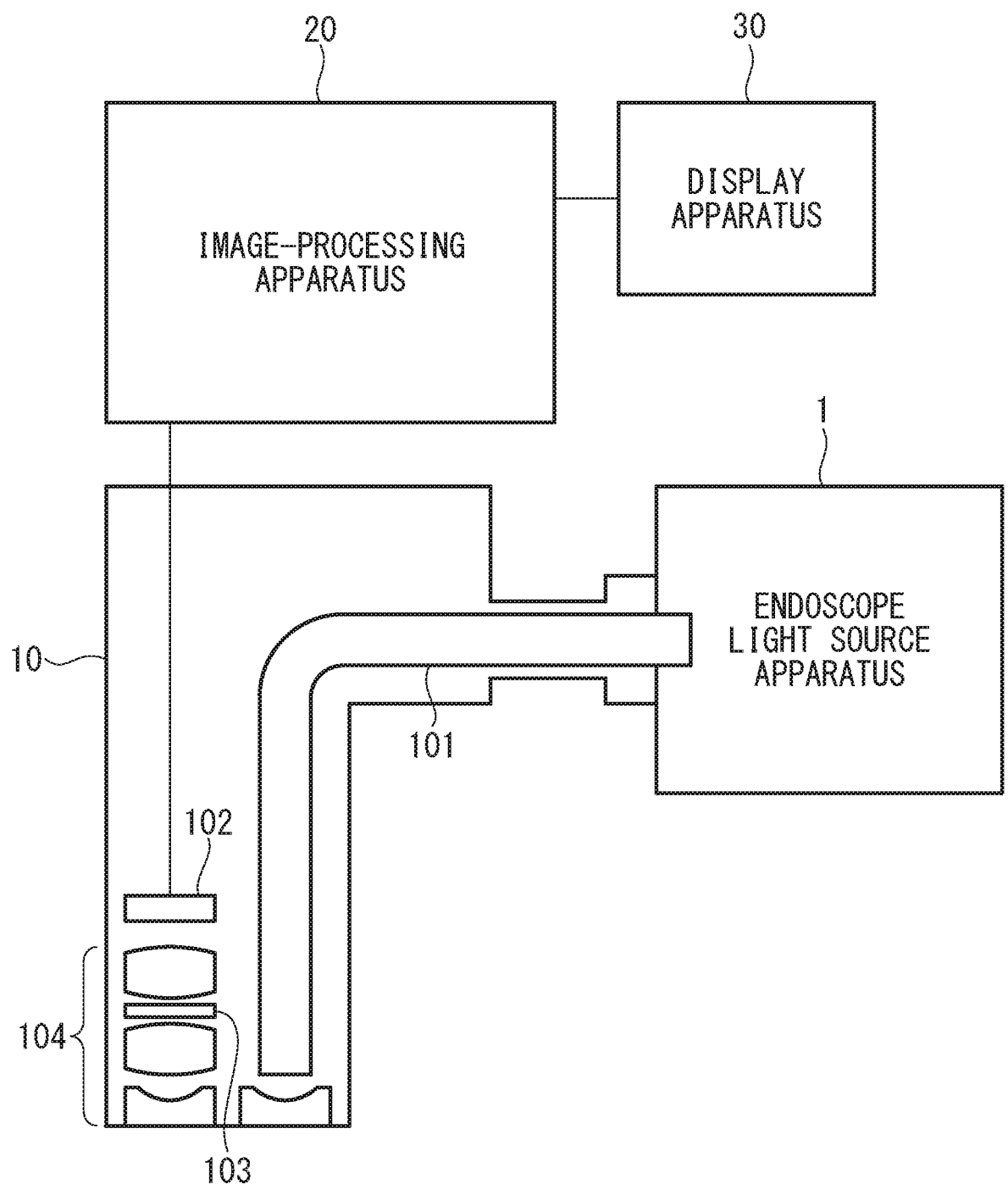
FIG. 1 is a diagram showing the overall configuration of an example of an endoscope system to which an endoscope light source apparatus according to an embodiment of the present invention is applied.

FIG. 1 shows an endoscope system to which the endoscope light source apparatus 1 according to this embodiment is applied. As shown in FIG. 1, the endoscope light source apparatus 1 is used by being connected to a fluorescence endoscope 10 and supplies illumination light beams for performing white-light observation and fluorescence observation to a light guide 101 of the fluorescence endoscope 10. Image signals acquired by an image-acquisition device 102 of the fluorescence endoscope 10 are transmitted to an image-processing apparatus 20, a white-light image and a fluorescence image are generated from the image signals in the image-processing apparatus 20, and the white-light image and the fluorescence image are displayed on a display apparatus 30.

The endoscope light source apparatus 1 can be attached to and detached from the fluorescence endoscope 10, and can be applied to a binocular-type fluorescence endoscope, as well as to a monocular-type fluorescence endoscope. The binocular-type fluorescence endoscope includes a white-light-observation-dedicated image-acquisition device and a fluorescence-observation-dedicated image-acquisition device. The monocular-type fluorescence endoscope includes a single image-acquisition device 102 that serves for performing both white-light observation and fluorescence observation. FIG. 1 shows an example of the monocular-type fluorescence endoscope 10.

In this embodiment, the fluorescence observation is assumed to be AFI (Auto Fluorescence Imaging) in which autofluorescence of 500 nm to 640 nm coming from a fluorescent substance such as collagen or the like is observed. In AFI, purple to blue excitation light beams of 390 nm to 470 nm and a green reference light beam of 540 nm to 560 nm are used. The autofluorescence intensity is decreased in tumor tissue as compared to normal tissue, whereas the intensities of reflected light of reference light are equivalent in tumor tissue and normal tissue. Therefore, it is possible to distinguish tumor tissue by detecting the autofluorescence and the reflected light of the reference light.

The autofluorescence intensity is weak and is approximately 1/500 to 1/100 of the excitation-light intensity. Therefore, the fluorescence endoscope 10, in which an excitation-light cut filter 103 that cuts excitation light is provided in a fluorescence-observation objective optical system 104, is used so that the image-acquisition device 102 can detect autofluorescence with good sensitivity.

Figure 2:
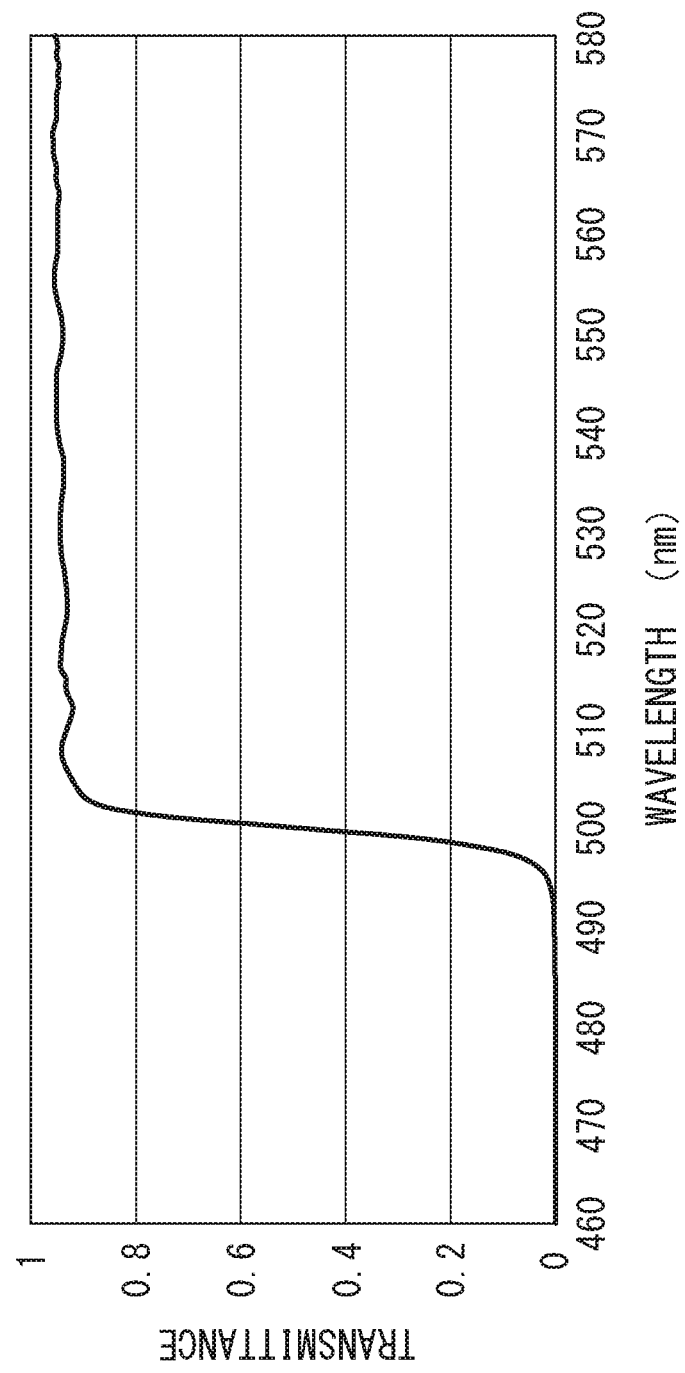
FIG. 2 is a graph showing light transmission characteristics of an excitation-light cut filter provided in a binocular-type fluorescence endoscope.

As shown in FIG. 2, the excitation-light cut filter for the binocular-type fluorescence endoscope blocks light of 390 nm to 470 nm and allows light having a wavelength that is equal to or greater than 500 nm to pass therethrough. Therefore, as the excitation light, it is possible to use light in a wide range from 390 nm to 470 nm.

Figure 3:
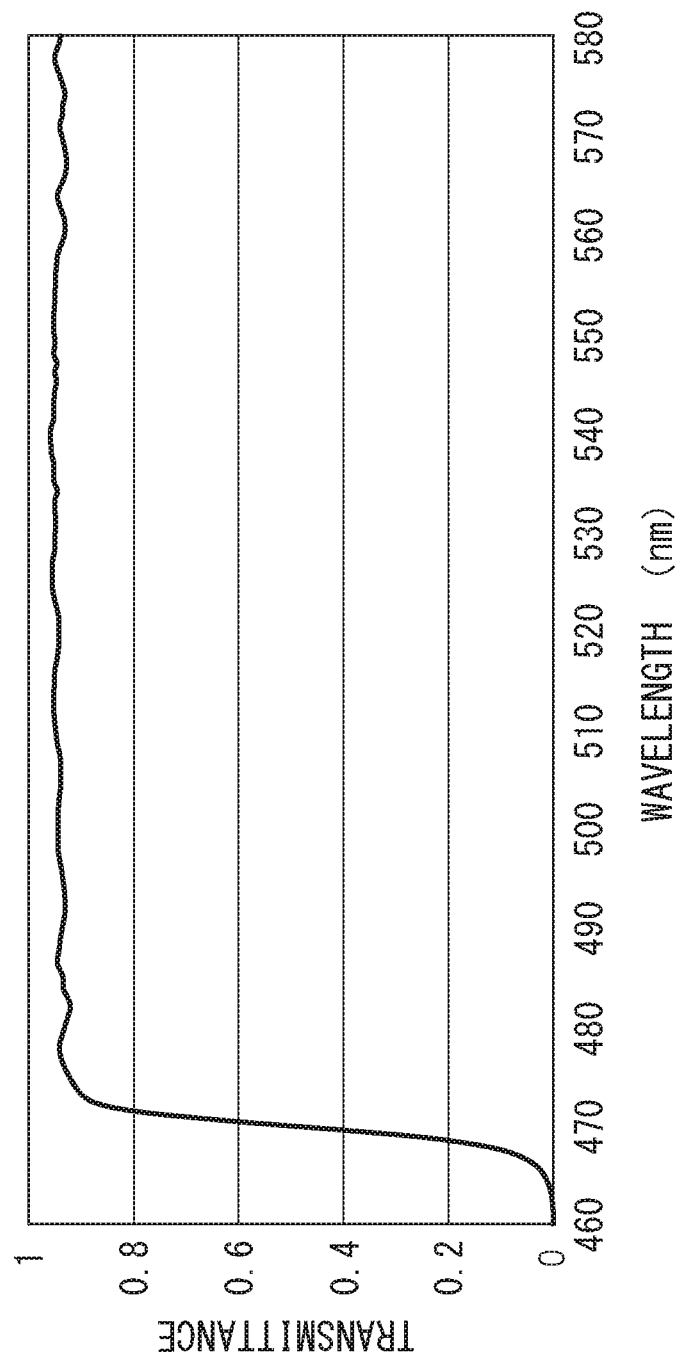
FIG. 3 is a graph showing light transmission characteristics of an excitation-light cut filter provided in a monocular-type fluorescence endoscope.

As shown in FIG. 3, the excitation-light cut filter for the monocular-type fluorescence endoscope blocks light of 390 nm to 440 nm and allows light having a wavelength that is equal to or greater than 470 nm to pass therethrough. Therefore, as the excitation light, light of 390 nm to 440 nm is used, and the blue wavelength band from 470 nm to 495 nm is used for white-light observation.

Figure 4:
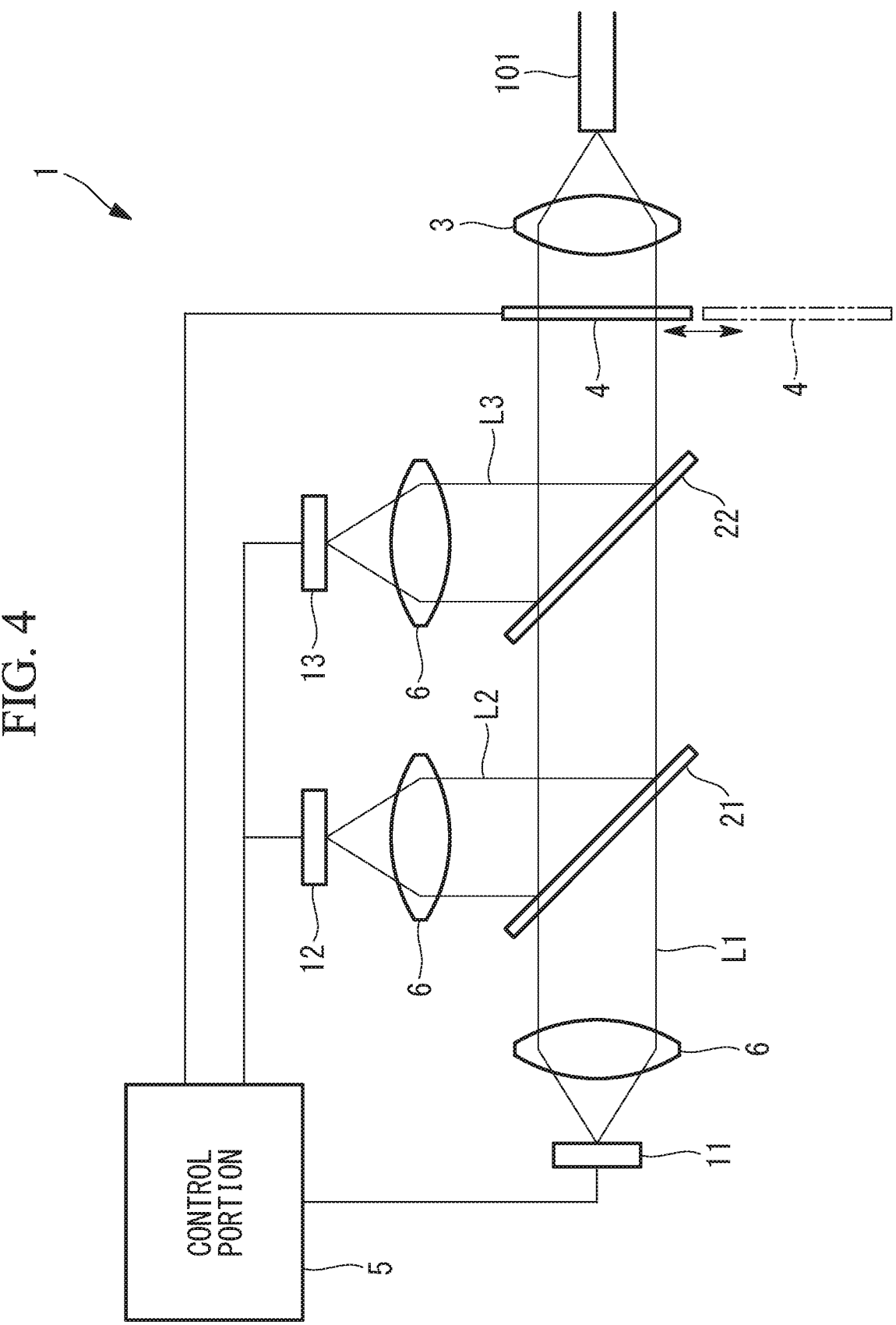
FIG. 4 is a diagram showing the overall configuration of the endoscope light source apparatus according to the embodiment of the present invention.

As shown in FIG. 4, the endoscope light source apparatus 1 is provided with: three solid-state light sources 11, 12, and 13; two optical members 21 and 22 that combine light beams L1, L2, and L3 output from the solid-state light sources 11, 12, and 13; a focusing optical system 3 that focuses the light combined by the optical members 21 and 22; an optical filter 4 that is provided so as to be insertable into/retractable from an optical path between the optical members 21 and 22 and the focusing optical system 3; and a control portion (controller) 5 that controls the turning on/off of the solid-state light sources 11, 12, and 13 and moving of the optical filter 4. The reference sign 6 indicates collimating lenses that individually convert the light beams L1, L2, and L3 output from the solid-state light sources 11, 12, and 13 to parallel light beams.

Figure 5:
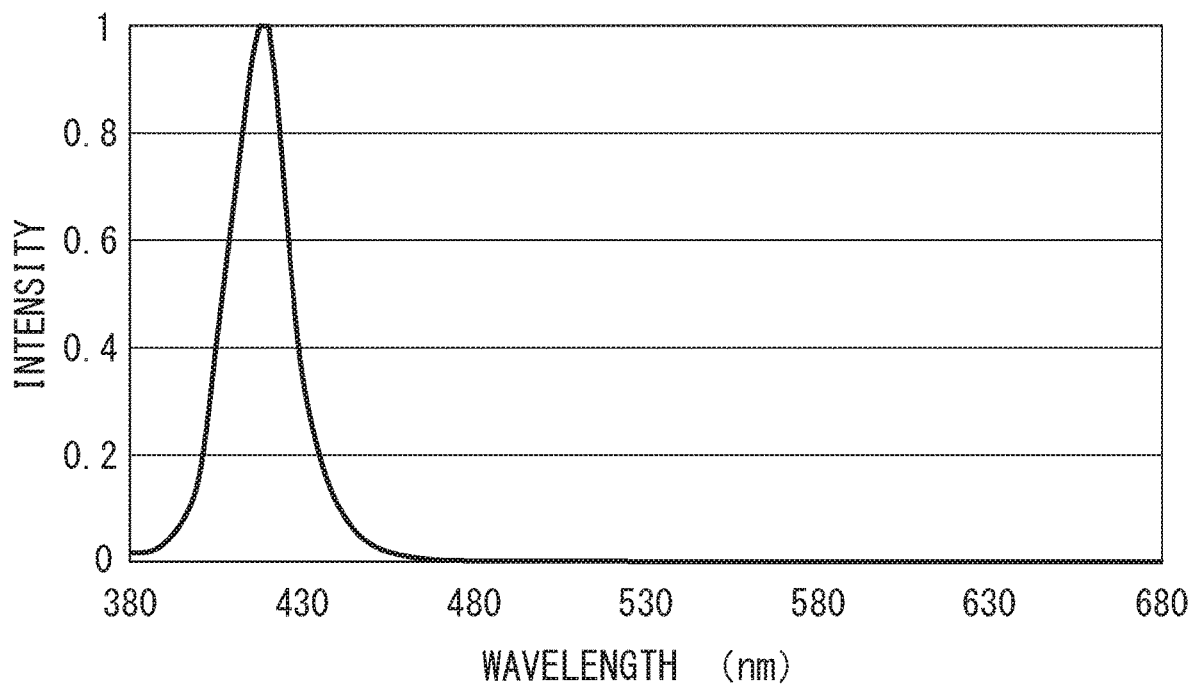
FIG. 5 is a diagram showing the spectrum of a first light beam output from a first solid-state light source in the endoscope light source apparatus in FIG. 4.
Figure 6:
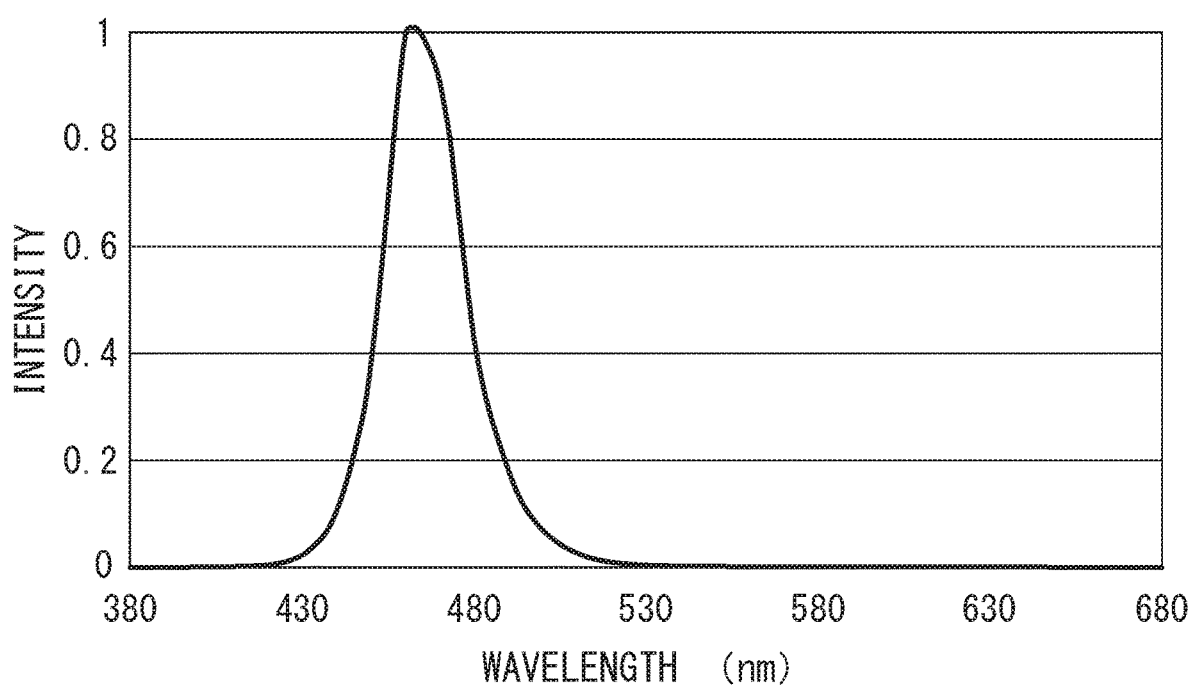
FIG. 6 is a diagram showing the spectrum of a second light beam output from a second solid-state light source in the endoscope light source apparatus in FIG. 4.

The first solid-state light source 11 and the second solid-state light source 12 are used for generating the excitation light. As shown in FIG. 5, the first solid-state light source 11 emits the purple first light beam L1 that mainly includes a first wavelength band from 390 nm to 440 nm. As shown in FIG. 6, the second solid-state light source 12 emits the blue second light beam L2 that mainly includes a second wavelength band from 440 nm to 470 nm. The first solid-state light source 11 and second solid-state light source 12 are formed of, for example, LEDs.

Figure 7:
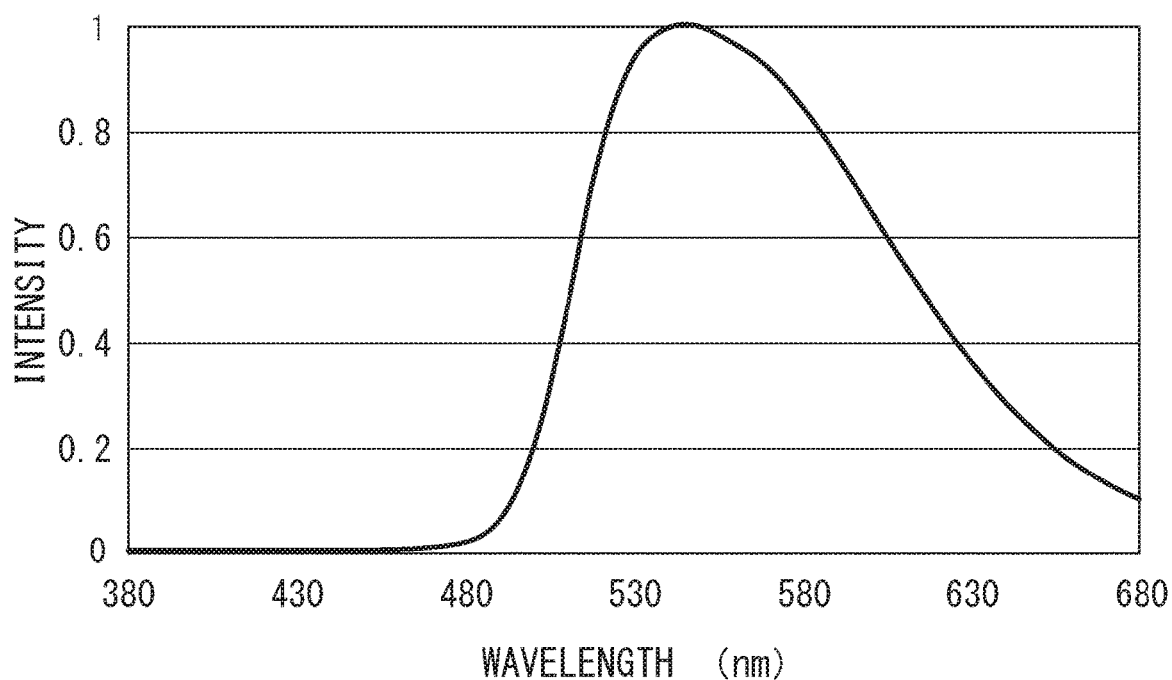
FIG. 7 is a diagram showing the spectrum of a third light beam output from a third solid-state light source in the endoscope light source apparatus in FIG. 4.

The third solid-state light source 13 is used for generating the reference light and the white light. As shown in FIG. 7, the third solid-state light source 13 emits the yellow third light beam L3 that mainly includes a wavelength band from green to red and that generates the white light by being mixed with the first light beam L1 and the second light beam L2. Therefore, the third light beam L3 includes a third wavelength band from 540 nm to 560 nm that corresponds to the reference light. The third solid-state light source 13 is formed, for example, by combining a blue LED and a yellow phosphor that emits yellow fluorescence by being excited by blue light emitted by the blue LED.

Figure 8:
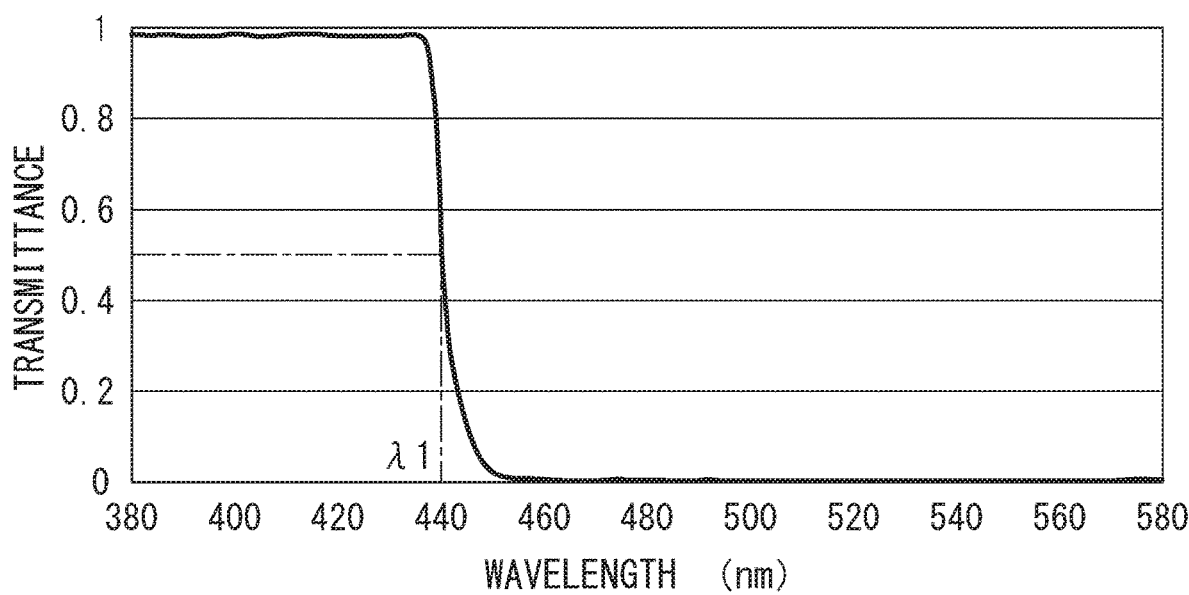
FIG. 8 is a diagram showing light transmission characteristics of a first optical member in the endoscope light source apparatus in FIG. 4.

The first optical member 21 is a beam combiner that has a first dichroic mirror surface. The first dichroic mirror surface allows the first light beam L1 to pass therethrough and reflects the second light beam L2, whereby the first light beam L1 and the second light beam L2 are combined. As shown in FIG. 8, the first dichroic mirror surface possesses a first cut-off wavelength $\lambda 1$ of 440 nm. The first cut-off wavelength $\lambda 1$ is a wavelength at which the light transmittance on the transmission-optical-path side of the first dichroic mirror surface becomes 50% and the first light beam L1 and the second light beam L2 overlap with each other.

The intensity of the combined light of the first and second light beams L1 and L2 generated by the first optical member 21 becomes extremely low at the first cut-off wavelength $\lambda 1$. The optical characteristics of the first optical member 21 are designed so that the combined light of the first and second light beams L1 and L2 has, at the first cut-off wavelength $\lambda 1$, an intensity that is equal to or greater than 10% of a maximum intensity.

Figure 9:
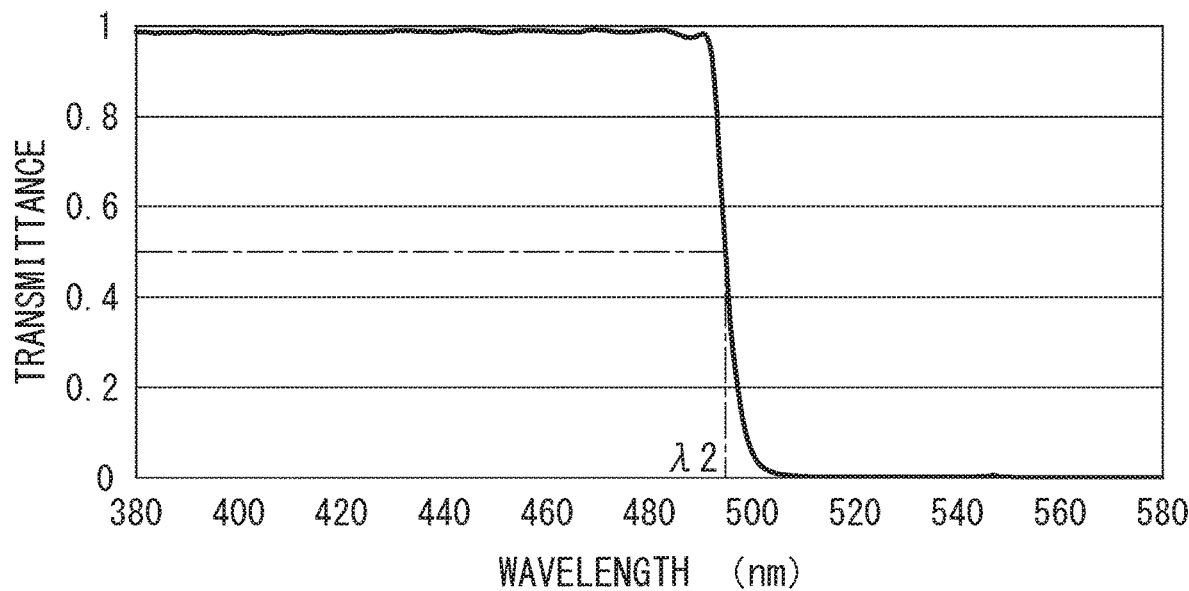
FIG. 9 is a diagram showing light transmission characteristics of a second optical member in the endoscope light source apparatus in FIG. 4.

The second optical member 22 is a beam combiner that has a second dichroic mirror surface. The second dichroic mirror surface allows the combined light of the first and second light beams L1 and L2 generated by the first optical member 21 to pass therethrough and reflects the third light beam L3, whereby the combined light beam of the first and second light beams L1 and L2 and the third light beam L3 are combined. As shown in FIG. 9, the second dichroic mirror surface possesses a second cut-off wavelength $\lambda 2$ of 495 nm. The second cut-off wavelength $\lambda 2$ is a wavelength at which the light transmittance on the transmission-optical-path side of the second dichroic mirror surface becomes 50% and the second light beam L2 and the third light beam L3 overlap with each other.

The intensity of the combined light of the first, second, and third light beams L1, L2, and L3 generated by the second optical member 22 becomes extremely low at the second cut-off wavelength $\lambda 2$. The optical characteristics of the second optical member 22 are designed so that the combined light of the first, second, and third light beams L1, L2, and L3 has, at the cut-off wavelength λ2, an intensity that is equal to or greater than 10% of the maximum intensity.

Figure 10:
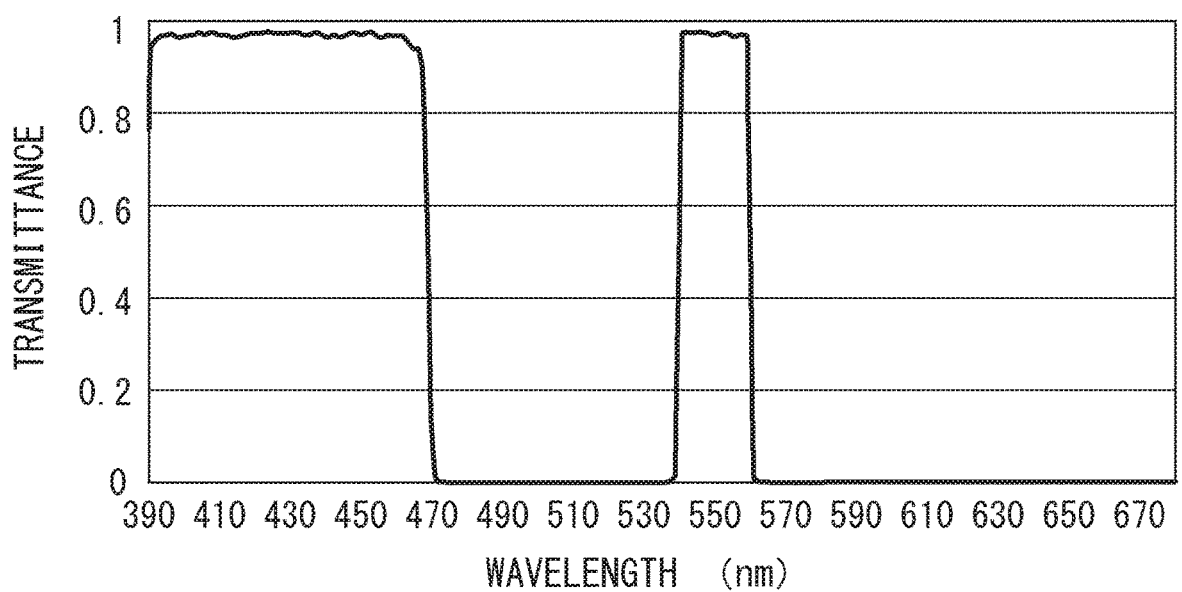
FIG. 10 is a diagram showing light transmission characteristics of an optical filter in the endoscope light source apparatus in FIG. 4.

The optical filter 4 is provided so as to be movable, by means of a moving mechanism (not shown), between a position in the optical path of the combined light generated by the second optical member 22 (see solid line in FIG. 4) and a position removed from the optical path (see two-dot chain line in FIG. 4). As shown in FIG. 10, the optical filter 4 selectively allows only light in two transmission bands to pass therethrough. The first transmission band is from 390 nm to 470 nm, corresponding to the first wavelength band and the second wavelength band, and the other transmission band is from 540 nm to 560 nm, corresponding to the third wavelength band. Therefore, when the optical filter 4 is inserted into the optical path, only the excitation light beam and the reference light beam are output from the endoscope light source apparatus 1 via the focusing optical system 3.

The optical characteristics of the first light beam L1 and the first dichroic mirror surface satisfy conditional expression (1) below. In expression (1), I1max is the maximum intensity of the first light beam L1 in the first wavelength band, I1 is the intensity of the first light beam L1 at a wavelength 10 nm or more away from the first wavelength band on a long-wavelength side thereof, and T1 is the light transmittance (%) of the first optical member 21 at a wavelength 10 nm or more away from the first wavelength band on a long-wavelength side thereof.

$$(I1/I1\ max) \times T1 \leq 0.01 \tag{1}$$

The optical characteristics of the second light beam L2 and the optical filter 4 satisfy conditional expression (2) below. In expression (2), I2max is the maximum intensity of the second light beam L2 in the second wavelength band, I2 is the intensity of the second light beam L2 at a wavelength 10 nm or more away from the second wavelength band on a long-wavelength side thereof, and T2 is the light transmittance (%) of the optical filter 4 at a wavelength 10 nm or more away from the second wavelength band on a long-wavelength side thereof.

$$(I2/I2\ max) \times T2 \leq 0.01 \tag{2}$$

Because the fluorescence is weaker as compared to the excitation light, when the excitation light includes a component at a long wavelength that overlaps with the transmission band of the excitation-light cut filter, the long-wavelength component of the excitation light acts as noise when incident on the image-acquisition device together with the fluorescence, thus causing the contrast of the fluorescence to be reduced. By satisfying conditional expression (1), the long-wavelength component (specifically, a component at a wavelength that is longer than 450 nm) included in the first light beam is satisfactorily removed by the first dichroic mirror surface, and thus, it is possible to enhance the contrast of the fluorescence. Similarly, by satisfying conditional expression (2), the long-wavelength component (specifically, a component at a wavelength that is longer than 480 nm) included in the second light beam is satisfactorily removed by the optical filter 4, and thus, it is possible to enhance the contrast of the fluorescence. Because the contrast of the fluorescence detected by the image-acquisition device with respect to noise is reduced when the values of conditional expressions (1) and (2) exceed 0.01, such a situation is not suitable for observing weak autofluorescence.

The focusing optical system 3 focuses the light that has passed through the optical filter 4. The focusing optical system 3 is designed so that a focal plane of the focusing optical system 3 is aligned with an incident surface of the light guide 101 when the endoscope light source apparatus 1 is connected to the fluorescence endoscope 10.

The control portion 5 has one type of illumination mode for performing white-light observation and two types of illumination modes for performing fluorescence observation, and controls, in one of the illumination modes, the turning on/off of the individual solid-state light sources 11, 12, and 13 and moving of the optical filter 4. The illumination mode to be executed by the control portion 5 can be determined by a user by means of, for example, a switch or the like (not shown).

Figure 11A:
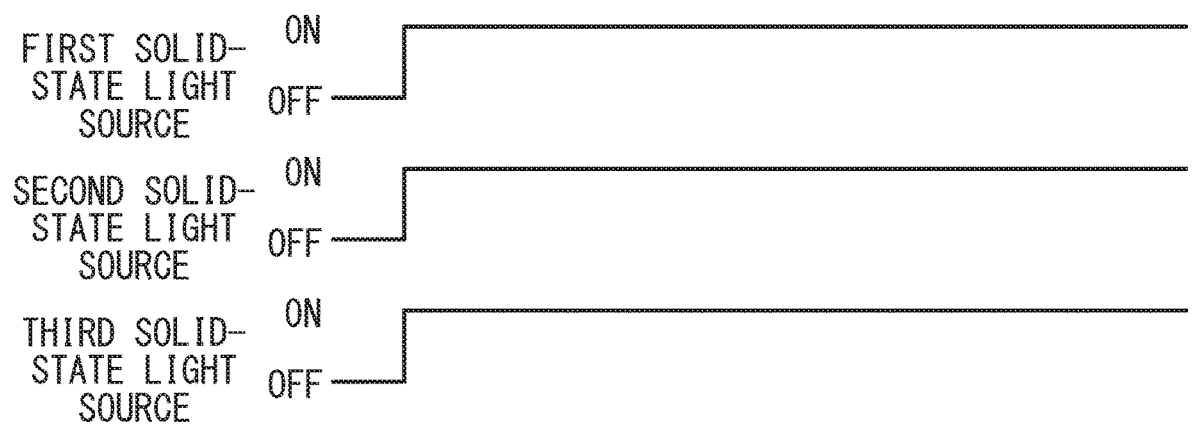
FIG. 11A is a diagram showing a timing chart indicating the operations of the first, second, and third solid-state light sources in a white-light illumination mode.
Figure 11B:
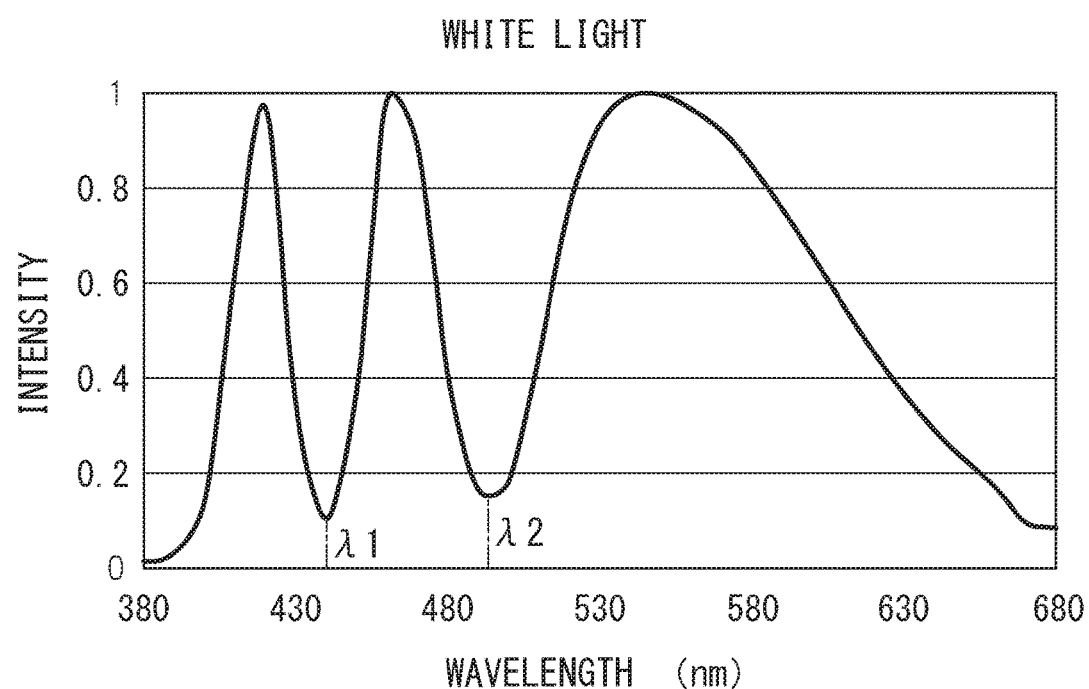
FIG. 11B is a diagram showing the spectrum of white light generated by the endoscope light source apparatus.

In "the white-light illumination mode" for performing white-light observation, the control portion 5 causes the optical filter 4 to be retracted to a position removed from the optical path, and, as shown in FIG. 11A, simultaneously turns on all of the first, second, and third solid-state light sources 11, 12, and 13. Therefore, as shown in FIG. 11A, white light is generated from the first, second, and third light beams L1, L2, and L3, and the white light is supplied to the light guide 101 from the endoscope light source apparatus 1.

Figure 12A:
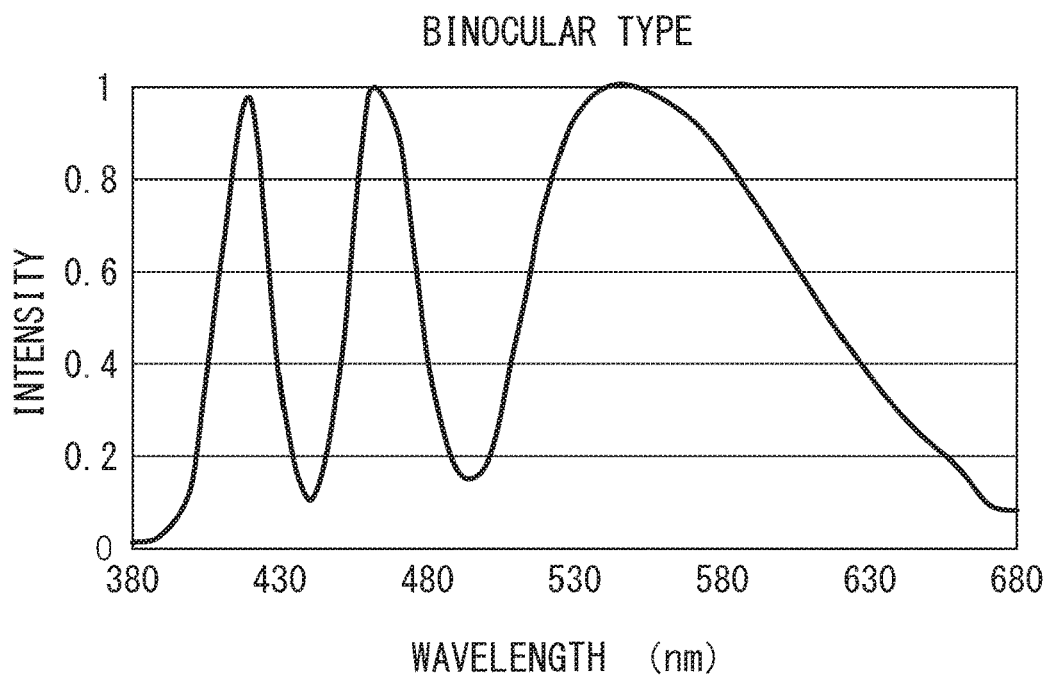
FIG. 12A is a diagram showing the spectrum of reflected light of white light, said reflected light being incident on an image-acquisition device in the binocular-type fluorescence endoscope, in the white-light illumination mode.
Figure 12B:
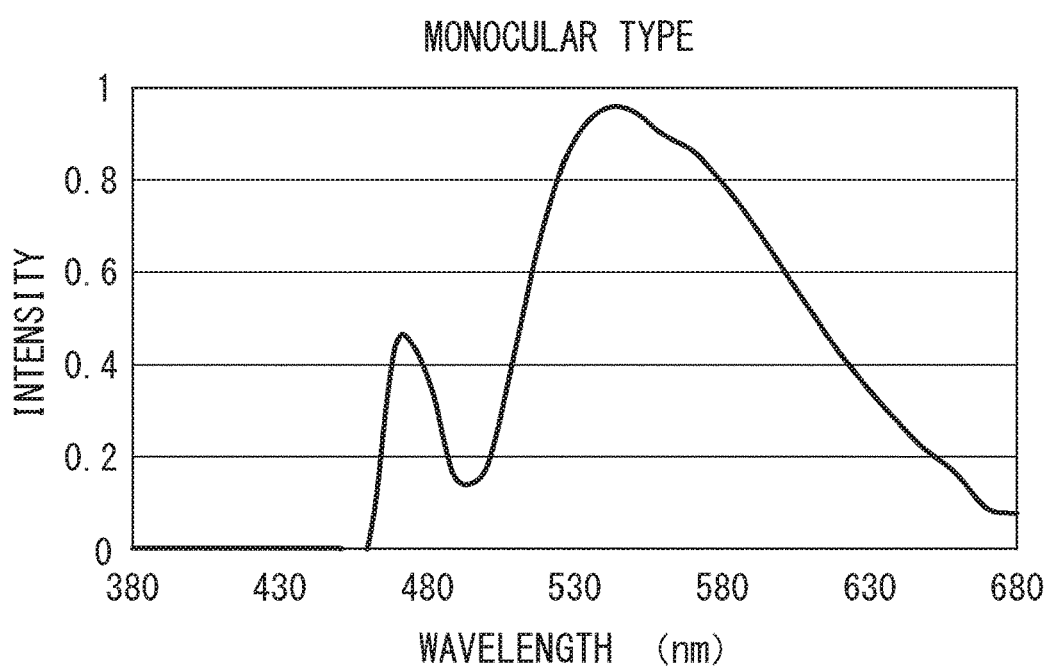
FIG. 12B is a diagram showing the spectrum of reflected light of white light, said reflected light being incident on an image-acquisition device of the monocular-type fluorescence endoscope, in the white-light illumination mode.

FIGS. 12A and 12B show the spectra of reflected light of the white light, said reflected light being incident on the white-light-observation color image-acquisition device, in "the white-light illumination mode". As shown in FIG. 12A, the reflected light of the white light output from the endoscope light source apparatus 1 is directly incident on the white-light-observation-dedicated image-acquisition device in the binocular-type fluorescence endoscope. On the other hand, as shown in FIG. 12B, reflected light in which light having a wavelength that is shorter than 470 nm has been cut by the excitation-light cut filter is incident on the image-acquisition device of the monocular-type fluorescence endoscope.

Here, as has been described above, although the white-light intensity becomes extremely low at the cut-off wavelengths λ1 and λ2, the white light possesses sufficiently high intensity also at the cut-off wavelengths λ1 and λ2. Therefore, it is possible to generate the white light without a missing wavelength, and thus, it is possible to perform white-light observation in which the color reproducibility of an imaging subject is high.

Figure 13A:
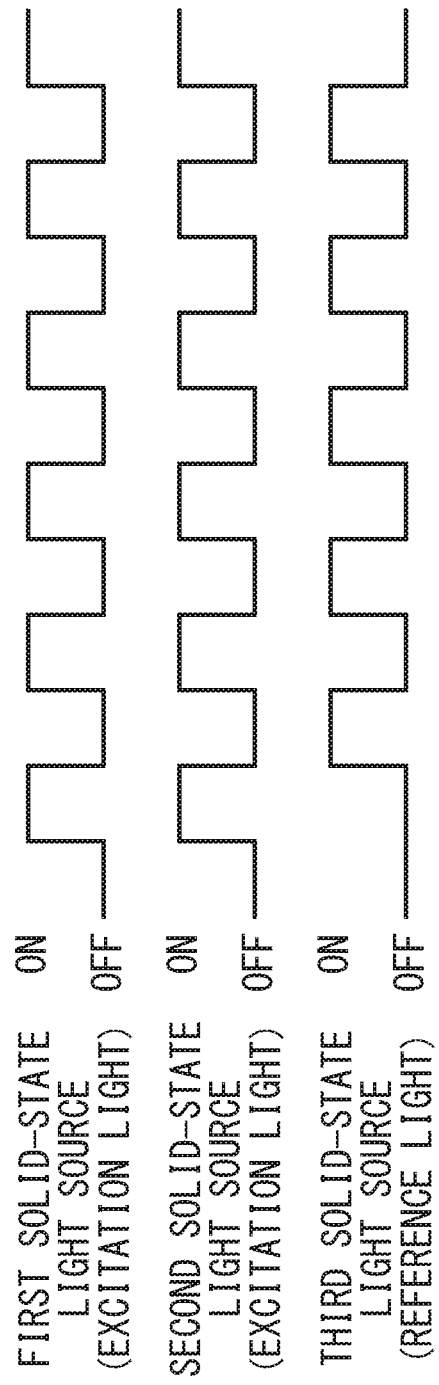
FIG. 13A is a diagram showing a timing chart indicating the operations of the first, second, and third solid-state light sources in a first excitation-light illumination mode.
Figure 13B:
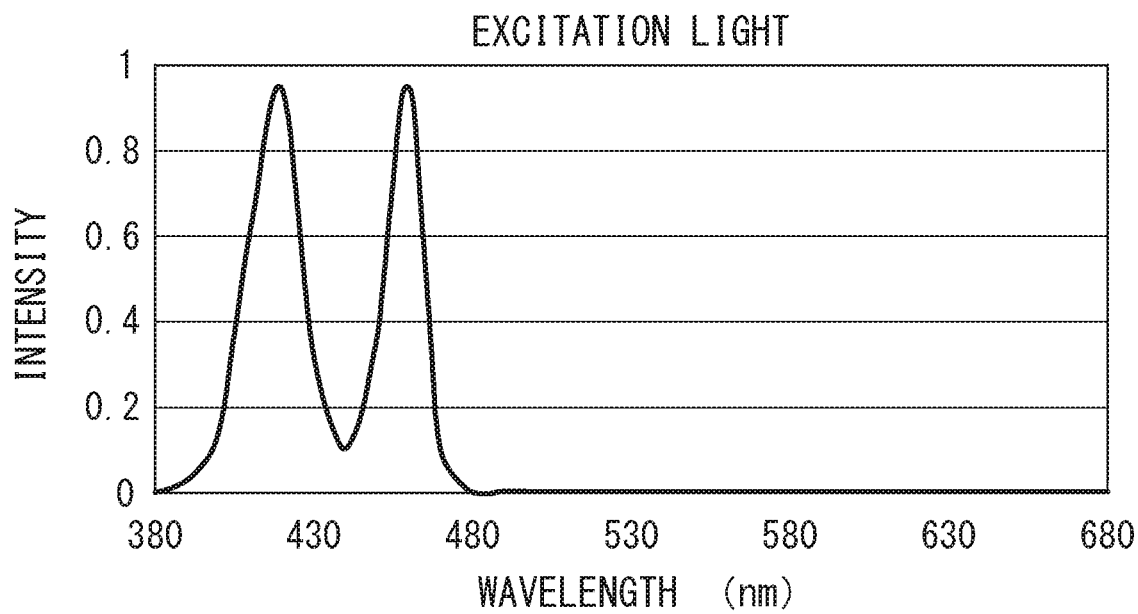
FIG. 13B is a diagram showing the spectrum of excitation light generated by the endoscope light source apparatus.
Figure 13C:
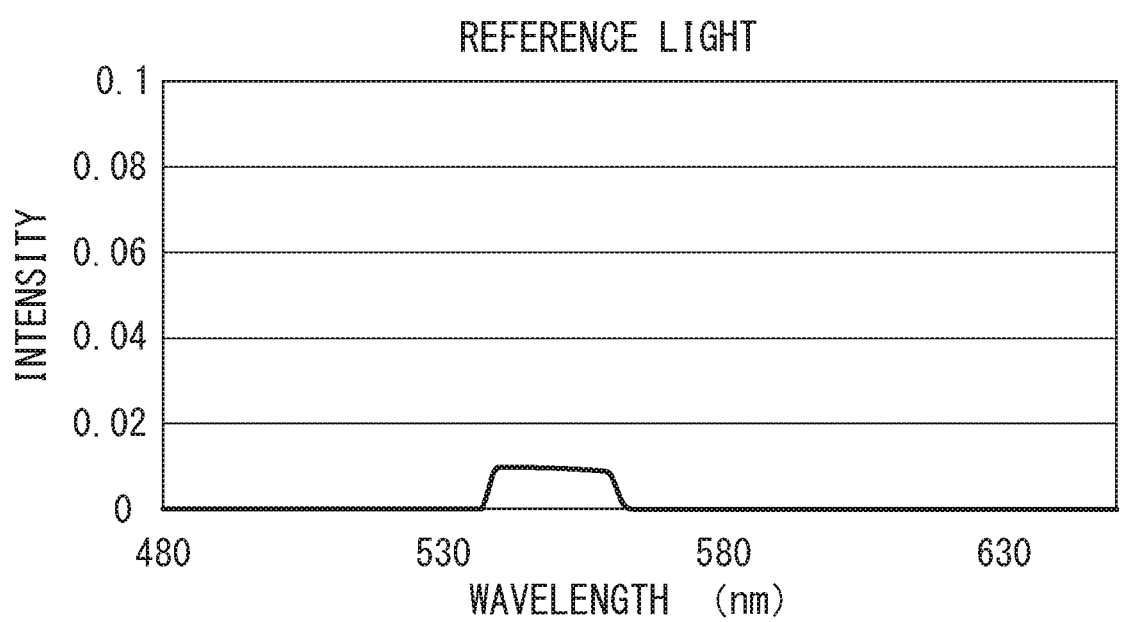
FIG. 13C is a diagram showing the spectrum of reference light generated by the endoscope light source apparatus.

The first fluorescence-observation illumination mode is "the first excitation-light illumination mode" for the binocular-type fluorescence endoscope, in which the first light beam L1 and the second light beam L2 are used as the excitation light. In "the first excitation-light illumination mode", the control portion 5 causes the optical filter 4 to be inserted into the optical path, and, as shown in FIG. 13A, turns on the first and second solid-state light sources 11 and 12 and the third solid-state light source 13 in an alternating manner. Therefore, the excitation light beams in the first and second wavelength bands and the reference light beam are generated in an alternating manner, and thus, the excitation light beams and the reference light beam are supplied to the light guide 101 from the endoscope light source apparatus 1 in an alternating manner. At this time, as shown in FIGS. 13B and 13C, the control portion 5 controls the output of the third solid-state light source 13 to be lower as compared to the outputs of the first and second solid-state light sources 11 and 12 so that the reference light becomes weaker than the excitation light (for example, so that the reference-light intensity becomes approximately 1/100 of the excitation-light intensity).

Figure 14A:
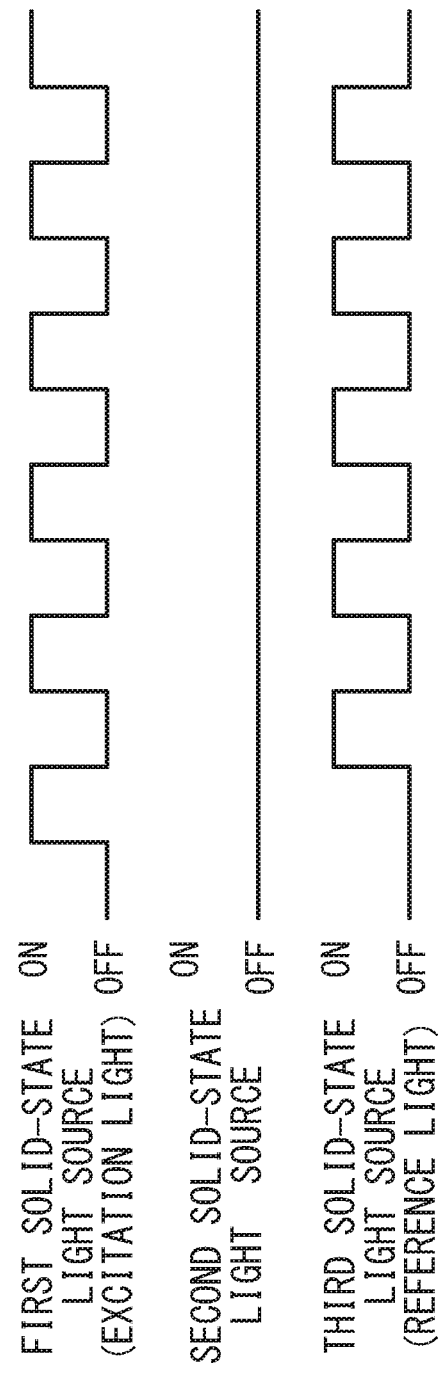
FIG. 14A is a diagram showing a timing chart indicating the operations of the first, second, and third solid-state light sources in a second excitation-light illumination mode.
Figure 14B:
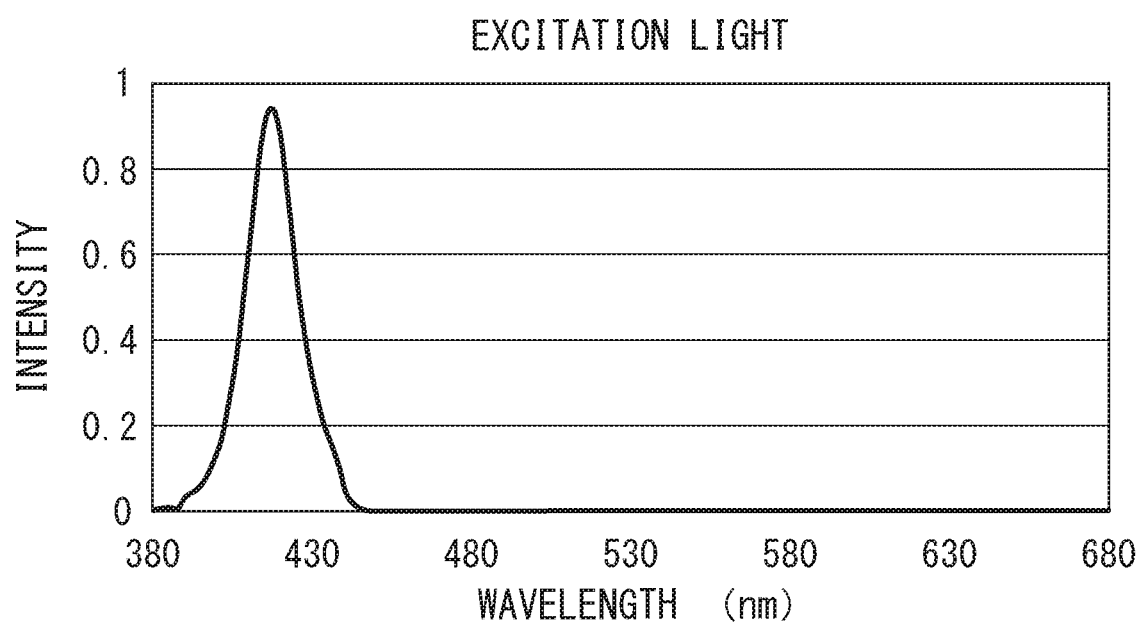
FIG. 14B is a diagram showing excitation light generated by the endoscope light source apparatus.
Figure 14C:
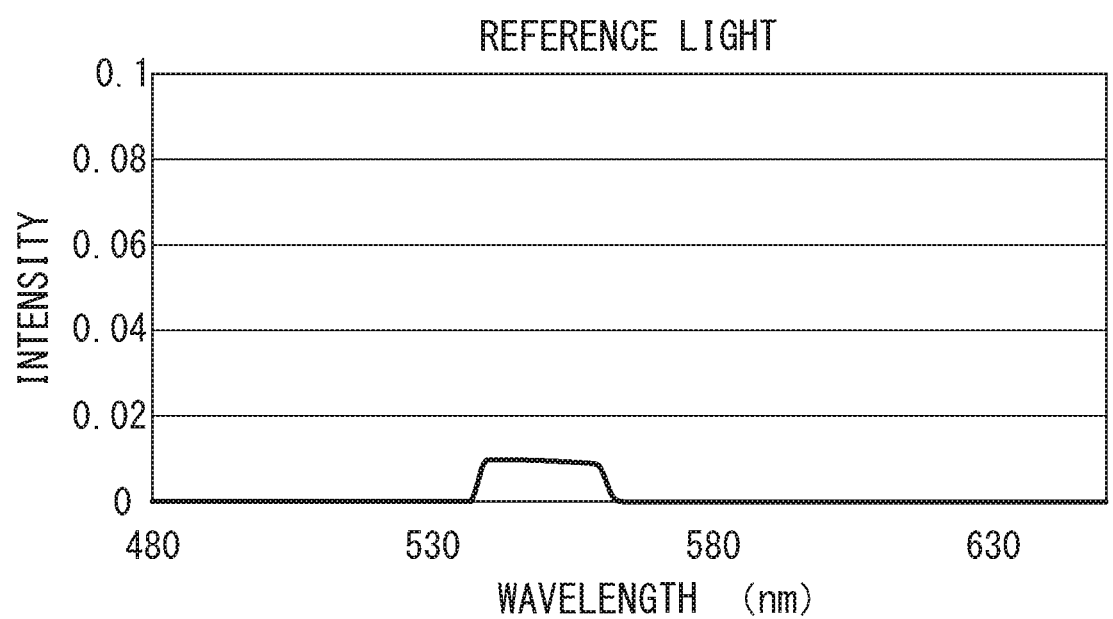
FIG. 14C is a diagram showing the spectrum of reference light generated by the endoscope light source apparatus.

The second fluorescence-observation illumination mode is "the second excitation-light illumination mode" for the monocular-type fluorescence endoscope, in which only the first light beam L1 is used as the excitation light. In "the second excitation-light illumination mode", the control portion 5 causes the optical filter 4 to be inserted into the optical path, and, as shown in FIG. 14A, turns off the second solid-state light source 12 and turns on the first solid-state light source 11 and the third solid-state light source 13 in an alternating manner. Therefore, the excitation light beam in the first wavelength band and the reference light beam are generated in an alternating manner, and thus, the excitation light beam and the reference light beam are supplied to the light guide 101 from the endoscope light source apparatus 1 in an alternating manner. At this time, as shown in FIGS. 14B and 14C, the control portion 5 controls the output of the third solid-state light source 13 to be lower as compared to the output of the first solid-state light source 11 so that the reference light becomes weaker than the excitation light (for example, so that the reference-light intensity becomes approximately $\frac{1}{100}$ of the excitation-light intensity).

Figure 15:
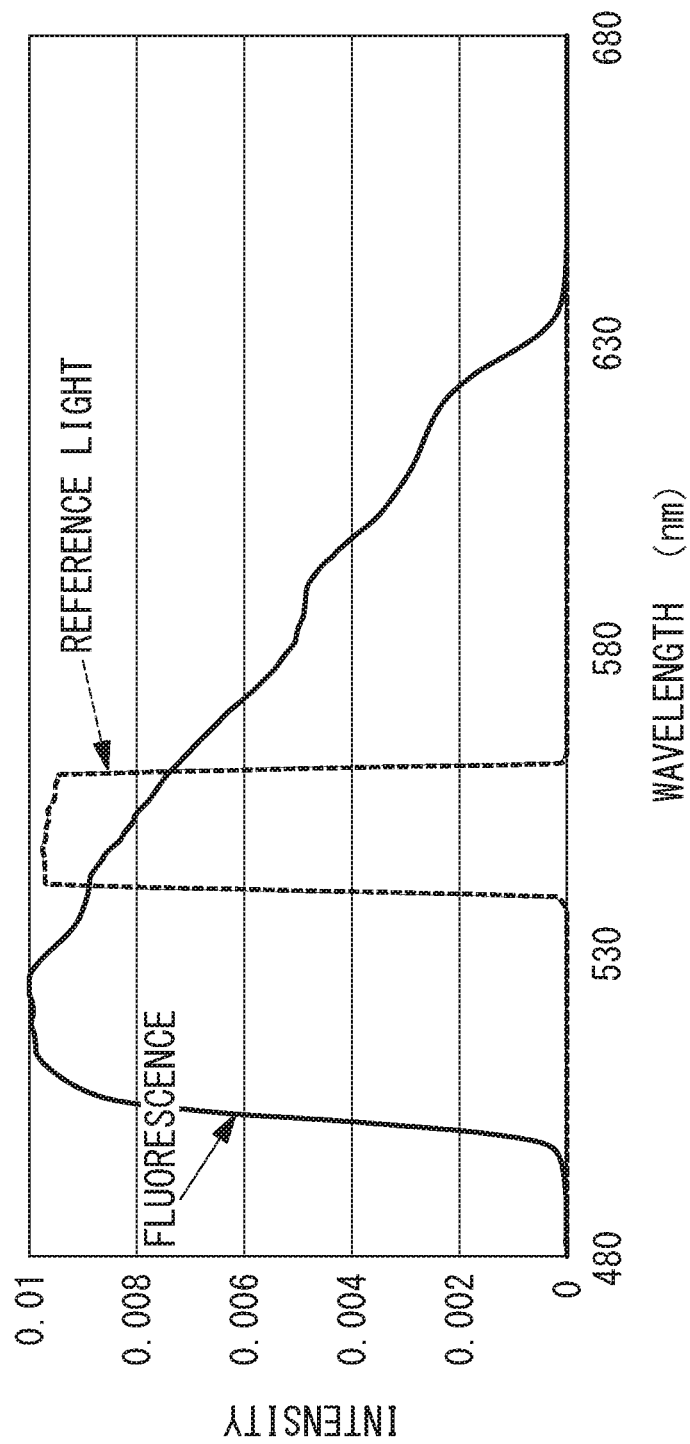
FIG. 15 is a diagram showing the spectra of fluorescence and a reflected light beam of reference light that are incident on the image-acquisition device of the fluorescence endoscope in the first excitation-light illumination mode.

FIG. 15 shows the spectra of the autofluorescence and the reflected light beam of the reference light that are incident on the fluorescence-observation image-acquisition device in "the first excitation-light illumination mode" and "the second excitation-light illumination mode". Because the excitation light beam and the reference light beam are radiated onto the imaging subject in an alternating manner, the autofluorescence and the reflected light beam of the reference light are incident on the image-acquisition device in an alternating manner. At this time, although the reflected light of the excitation light enters the objective optical system 104 together with the autofluorescence, the reflected light of the excitation light is cut by the excitation-light cut filter, and thus, only the autofluorescence is incident on the image-acquisition device.

Next, the operation of the thus-configured endoscope light source apparatus 1 will be described.

In the case in which the endoscope light source apparatus 1 is used by being connected to the binocular-type fluorescence endoscope, one of "the white-light illumination mode" and "the first excitation-light illumination mode" is selected.

When "the white-light illumination mode" is selected, the optical filter 4 is retracted from the optical path, and the first, second, and third light beams L1, L2, and L3 are simultaneously output from the first, second, and third solid-state light sources 11, 12, and 13, thereby supplying the white light to the light guide 101 from the endoscope light source apparatus 1. The white light is radiated onto the imaging subject via the light guide 101, is reflected at the imaging subject, and is made incident on the white-light-observation-dedicated color image-acquisition device. By doing so, it is possible to perform white-light observation of the imaging subject by means of the fluorescence endoscope 10.

When "the first excitation-light illumination mode" is selected, the optical filter 4 is inserted into the optical path, and the first and second light beams L1 and L2 and the third light beam L3 are output from the first and second solid-state light sources 11 and 12 and the third solid-state light source 13 in an alternating manner, thereby supplying the excitation light and the reference light to the light guide 101 from the endoscope light source apparatus 1 in an alternating manner. The excitation light beam and the reference light beam are radiated onto the imaging subject in an alternating manner, and thus, the autofluorescence and the reflected light beam of the reference light are incident on the fluorescence-observation-dedicated image-acquisition device in an alternating manner. By doing so, it is possible to perform autofluorescence observation of the imaging subject by means of the fluorescence endoscope 10.

On the other hand, in the case in which the endoscope light source apparatus 1 is used by being connected to the monocular-type fluorescence endoscope 10, one of "the white-light illumination mode" and "the second excitation-light illumination mode" is selected.

When "the white-light illumination mode" is selected, as with the case of the binocular-type fluorescence endoscope, the white light is supplied to the light guide 101 from the endoscope light source apparatus 1, thus irradiating the imaging subject. The white light reflected at the imaging subject passes through the excitation-light cut filter 103, which causes the light having a wavelength that is shorter than 470 nm be cut therefrom, and is incident on the color image-acquisition device 102. By doing so, it is possible to perform white-light observation of the imaging subject by means of the fluorescence endoscope 10.

When "the second excitation-light illumination mode" is selected, the optical filter 4 is inserted into the optical path, and the first light beam L1 and the third light beam L3 are output from the first solid-state light source 11 and the third solid-state light source 13 in an alternating manner, thereby supplying the excitation light and the reference light to the light guide 101 from the endoscope light source apparatus 1 in an alternating manner. The excitation light beam and the reference light beam are radiated onto the imaging subject in an alternating manner, and thus, the autofluorescence and the reflected light of the reference light are incident on the image-acquisition device 102 via the excitation-light cut filter 103 in an alternating manner. By doing so, it is possible to perform autofluorescence observation of the imaging subject by means of the fluorescence endoscope 10.

As has been described above, with this embodiment, the first solid-state light source 11 that emits the short-wavelength excitation light and the second solid-state light source 12 that emits the long-wavelength excitation light are provided as the excitation-light light sources. By doing so, the two types of illumination modes that are suitable for fluorescence observation by means of the monocular-type fluorescence endoscope and fluorescence observation by means of the binocular-type fluorescence endoscope, respectively, are realized just by switching between turning on and off the second solid-state light source 12. In other words, an optical filter is not necessary to switch between the two types of illumination modes for performing fluorescence observation, and only the optical filter 4 for switching between the white-light-observation illumination mode and the fluorescence-observation illumination mode is sufficient as the optical filter needed in the endoscope light source apparatus 1. In general, the sizes of the solid-state light sources 11, 12, and 13, such as LEDs, are approximately 3 mm×3 mm, whereas the diameter of an optical filter is approximately 40 mm. By decreasing the number of such large optical filters, it is possible to effectively reduce the size of the endoscope light source apparatus 1, particularly in the height direction (the direction that intersects the optical axis of the first light beam L1 in FIG. 4).

Figure 16:
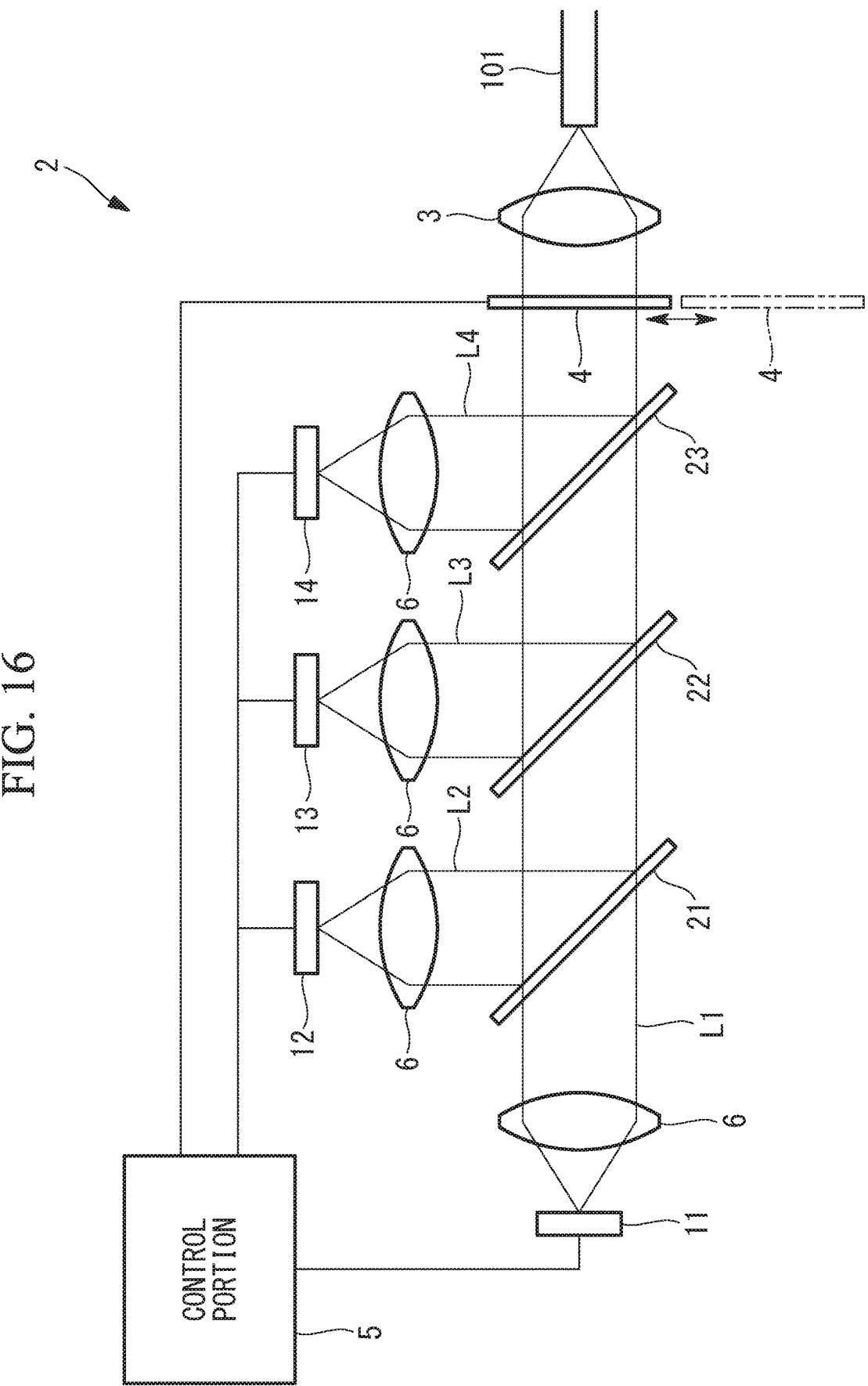
FIG. 16 is a diagram showing the overall configuration of a modification of the endoscope light source apparatus in FIG. 4.
Figure 17:
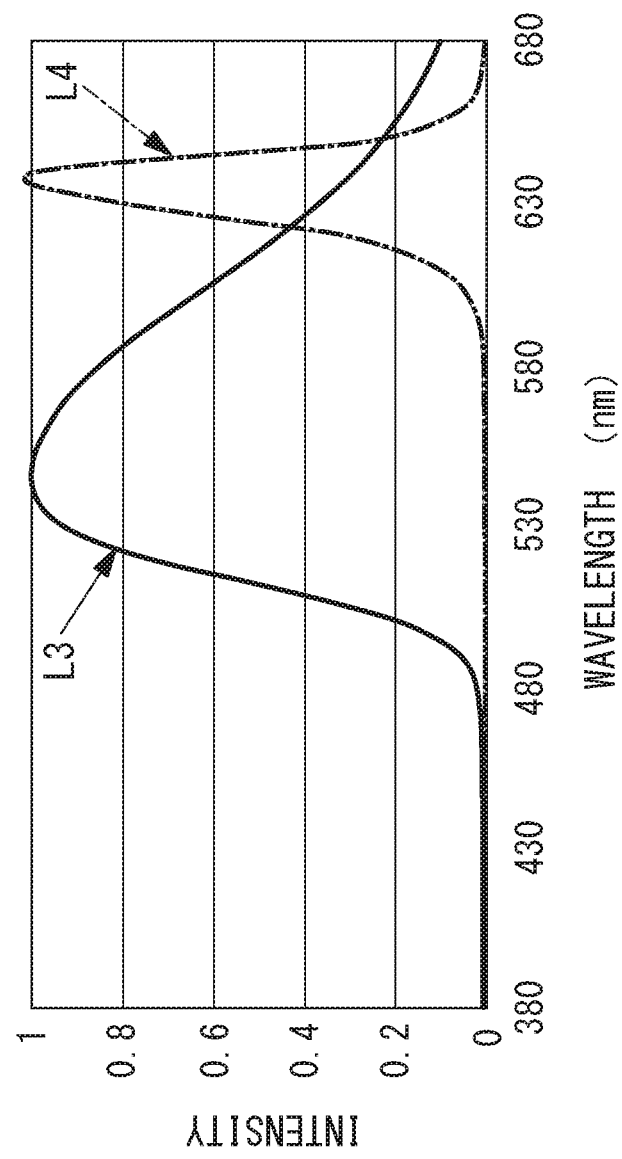
FIG. 17 is a diagram showing the spectrum of a fourth light beam output from a fourth solid-state light source in the endoscope light source apparatus in FIG. 16.

As shown in FIGS. 16 and 17, the above-described embodiment may be additionally provided with a fourth solid-state light source 14 that emits a red fourth light beam L4, and white light may be generated from the first, second, third, and fourth light beams L1, L2, L3, and L4. In this case, a third optical member 23 is additionally provided in order to combine the fourth light beam L4 with the combined light of the first, second, and third light beams L1, L2, and L3 generated by the first and second optical members 21 and 22.

Figure 18:
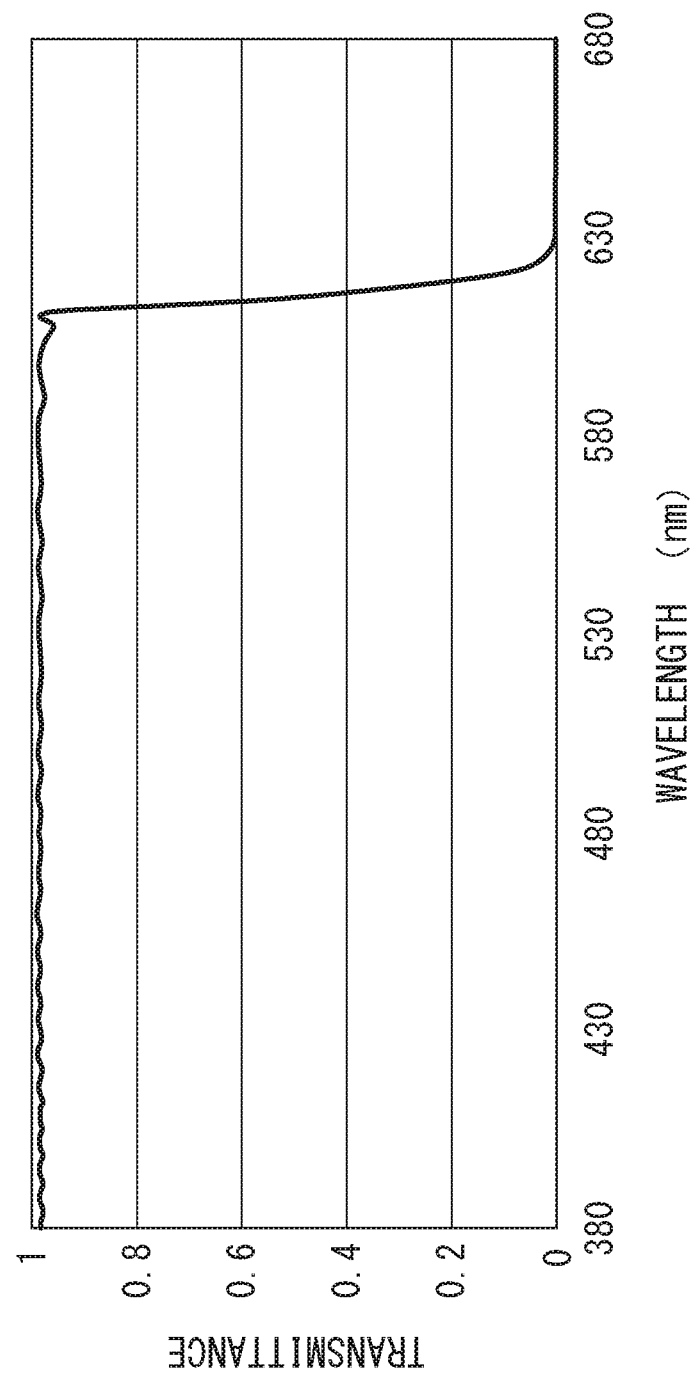
FIG. 18 is a diagram showing light transmission characteristics of a third optical member of the endoscope light source apparatus in FIG. 16.

The third optical member 23 is a beam combiner that has a third dichroic mirror surface. As shown in FIG. 18, the third dichroic mirror surface possesses a cut-off wavelength of 615 nm, allows the first, second, and third light beams L1, L2, and L3 to pass therethrough, and reflects the fourth light beam L4.

In "the white-light illumination mode", the control portion 5 simultaneously turns on the fourth solid-state light source 14 in addition to the first, second, and third solid-state light sources 11, 12, and 13. The control performed by the control portion 5 in "the first excitation-light illumination mode" and "the second excitation-light illumination mode" is the same as that described above.

With this modification, by generating the white light that includes the red fourth light beam L4 by additionally providing the fourth solid-state light source 14, it is possible to further increase the color reproducibility of the imaging subject when performing white-light observation.

In the above-described embodiment, the color image-acquisition device is assumed to be used for performing white-light observation, and a simultaneous method in which the light beams L1, L2, and L3 of three colors are simultaneously radiated onto the imaging subject is assumed to be employed in "the white-light illumination mode"; however, a frame sequential method may be employed in the case in which a monochromatic image-acquisition device is used for performing white-light observation.

Figure 19B:
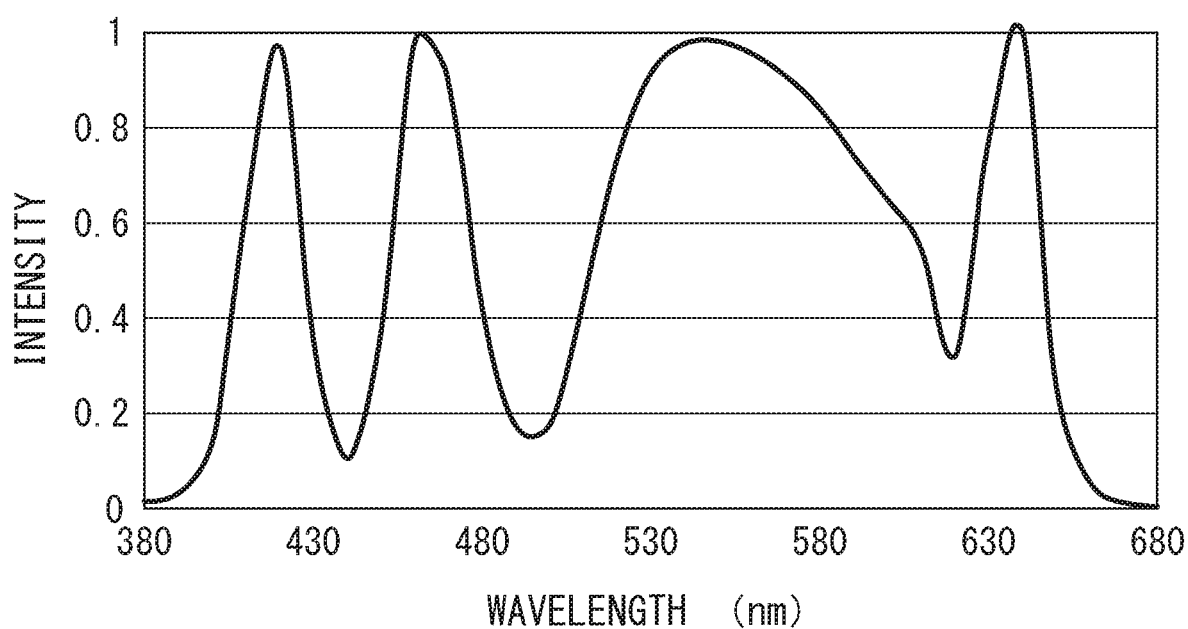
FIG. 19B is a diagram showing the spectrum of white light generated by the endoscope light source apparatus.

In "the white-light illumination mode" based on the frame sequential method performed by means of an endoscope light source apparatus 2 in FIG. 16, the control portion 5 sequentially turns on the first and second solid-state light sources 11 and 12, the third solid-state light source 13, and the fourth solid-state light source 14, as shown in FIG. 19A. By doing so, as shown in FIG. 19B, the purple and blue first and second light beams L1 and L2, the yellow third light beam L3, and the red fourth light beam L4 are sequentially supplied to the light guide 101 from the endoscope light source apparatus 2. FIG. 19B shows the spectrum of the white light generated from the first, second, third, and fourth light beams L1, L2, L3, and L4.

Figure 20A:
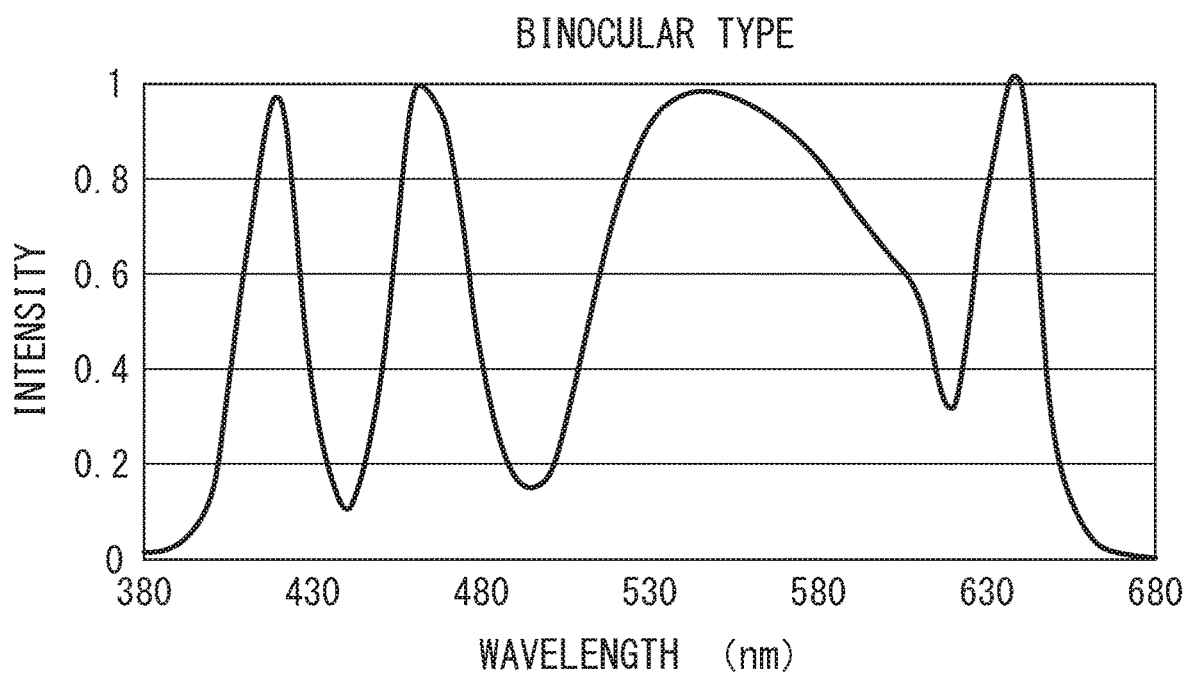
FIG. 20A is a diagram showing the spectrum of reflected light that is incident on the image-acquisition device of the binocular-type fluorescence endoscope in the white-light illumination mode.
Figure 20B:
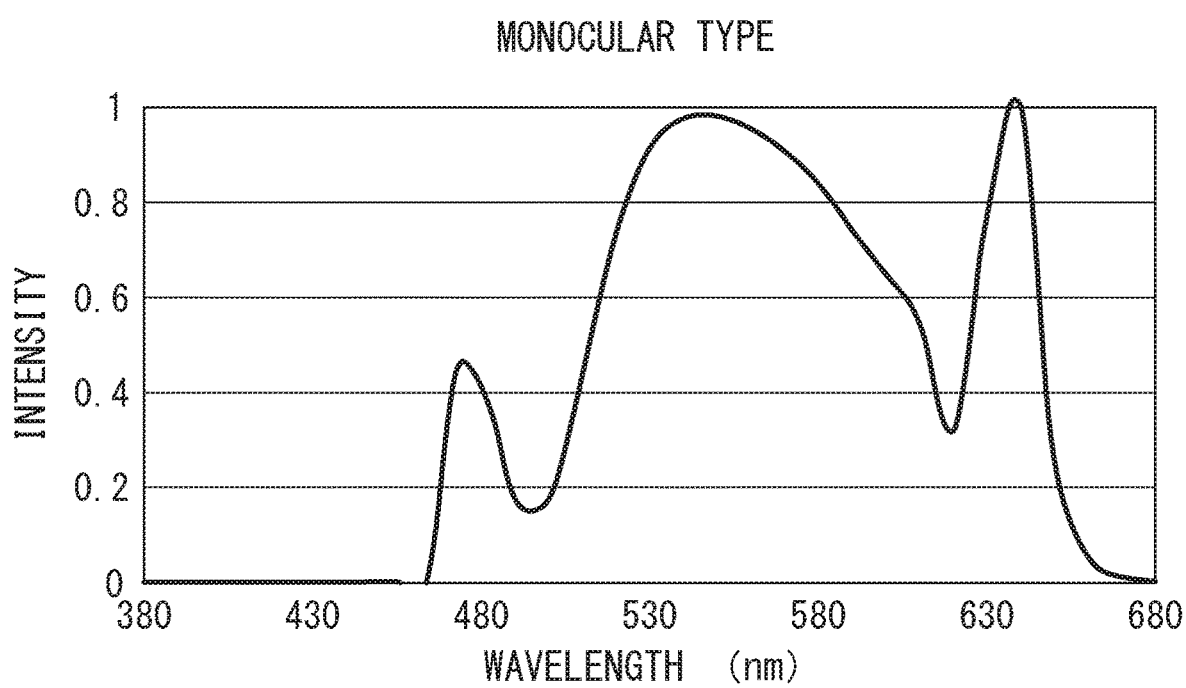
FIG. 20B is a diagram showing the spectrum of reflected light that is incident on the image-acquisition device of the monocular-type fluorescence endoscope in the white-light illumination mode.

As shown in FIG. 20A, the reflected light of the first, second, third, and fourth light beams L1, L2, L3, and L4 supplied to the light guide 101 from the endoscope light source apparatus 2 is directly incident on the white-light-observation-dedicated image-acquisition device of the binocular-type fluorescence endoscope. On the other hand, as shown in FIG. 20B, the reflected light in which the light having a wavelength that is shorter than 470 nm has been cut by the excitation-light cut filter is incident on the image-acquisition device of the monocular-type fluorescence endoscope.

In "the first excitation-light illumination mode" and "the second excitation-light illumination mode", the control portion 5 controls the first, second, and third solid-state light sources 11, 12, and 13 and the optical filter 4 in a similar manner to that in the control described above, and, furthermore, turns off the fourth solid-state light source 14.

Figure 21:
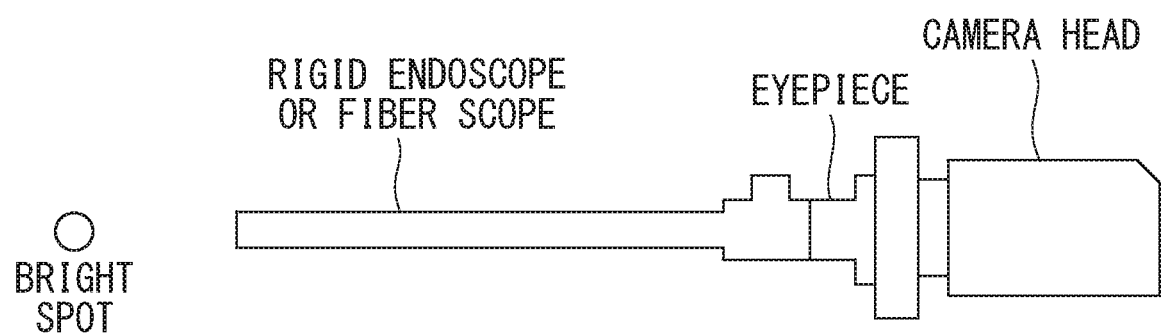
FIG. 21 is a diagram showing an example of an endoscope to which the endoscope light source apparatus according to the embodiment of the present invention is applied.
Figure 22:
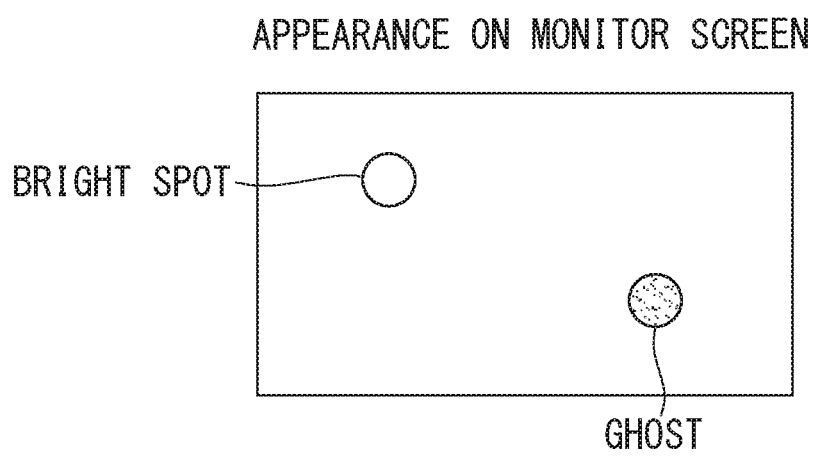
FIG. 22 is a diagram showing a case in which a ghost appears when performing observation by using the endoscope in FIG. 21.

In the above-described embodiment, in the case in which an endoscope in which a rigid endoscope, a fiber scope, or the like is connected to a camera head via an eyepiece is used (see FIG. 21), if a bright spot (reflected light generated when light hits a treatment tool such as forceps or the like or halation or the like due to specular reflected light coming from a living organism) is generated, there are cases in which an image of light that should not be observed to begin with, which is referred to as a ghost that hinders observation, appears at a position that is substantially symmetrical to that of the bright spot (see FIG. 22).

A mechanism by which a ghost is generated will be described below.

Figure 23:
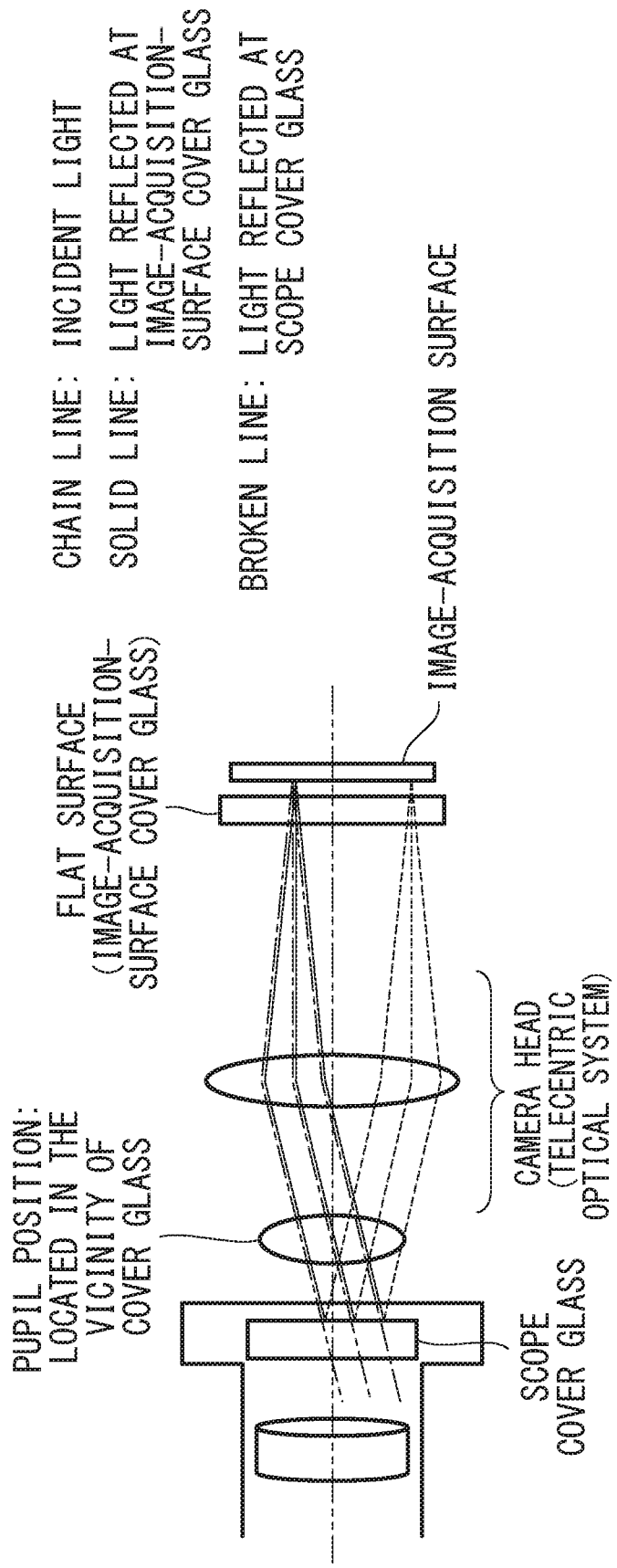
FIG. 23 is a diagram showing, in the endoscope in FIG. 21, optical paths and image formation positions of incident light and reflected light when a ghost is generated.

The light that has entered the camera head from the scope forms an image on an image-acquisition surface by means of a camera-head optical system (see chain line in FIG. 23). The camera-head optical system is configured to be a substantially telecentric optical system for the purpose of reducing shading or reducing color shading in the case of being used in combination with a three-plane image-acquisition device. At this time, although a portion of the light rays forming an image is reflected in the case in which an image-acquisition-surface cover glass is not coated, because the telecentric optical system is employed, the reflected light returns to a scope cover glass through substantially the same optical path as that of the incident light (see solid line in FIG. 23).

Because the scope cover glass is not coated in order to ensure sufficient resistance to being autoclaved or the like, the reflectance thereof is high, and thus, the light is reflected again. Because the pupil position is at a position that is close to the scope cover glass, a large portion of the reflected light is reflected at the cover glass, passes through the camera-head optical system again, and forms an image at a position that is substantially symmetrical to the normal image formation position, thus forming a ghost (see broken line in FIG. 23).

In order to eliminate such a problem, in this embodiment, an anti-reflection film may be provided on the reflection surface that causes a ghost to be generated, specifically, a non-coated flat surface in the vicinity of the image-acquisition surface on a camera-head side.

Figure 24:
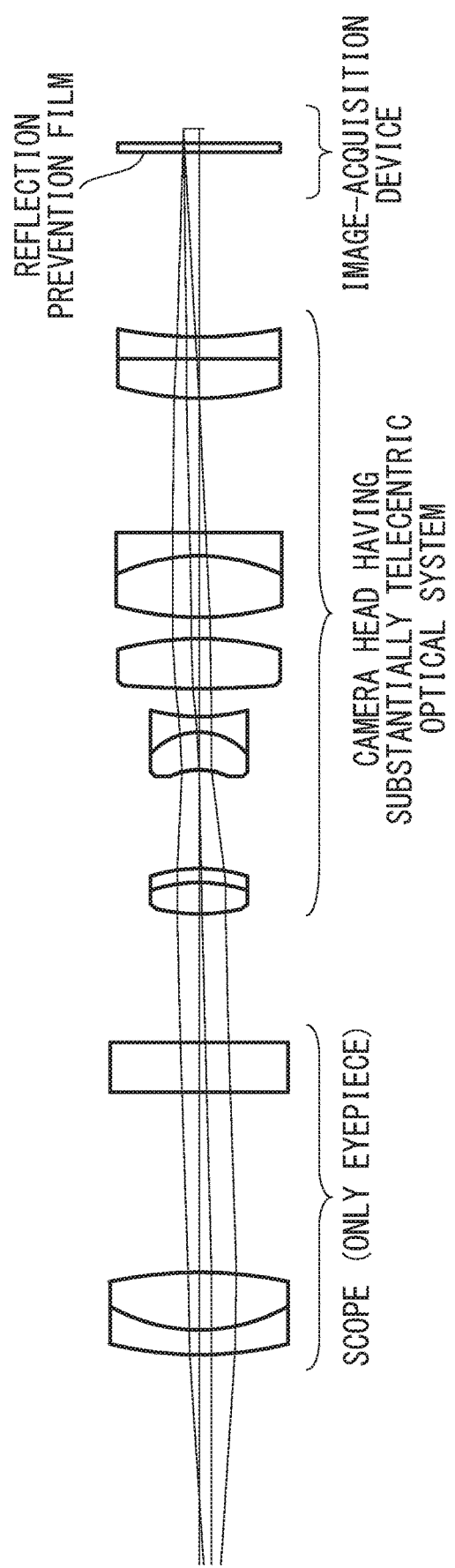
FIG. 24 is a diagram showing a case in which a reflection prevention film is provided in the vicinity of an image-acquisition device in the endoscope in FIG. 21.

By doing so, the reflected light is prevented from being generated, and thus, it is possible to suppress the appearance of a ghost (see FIG. 24).

Figure 25:
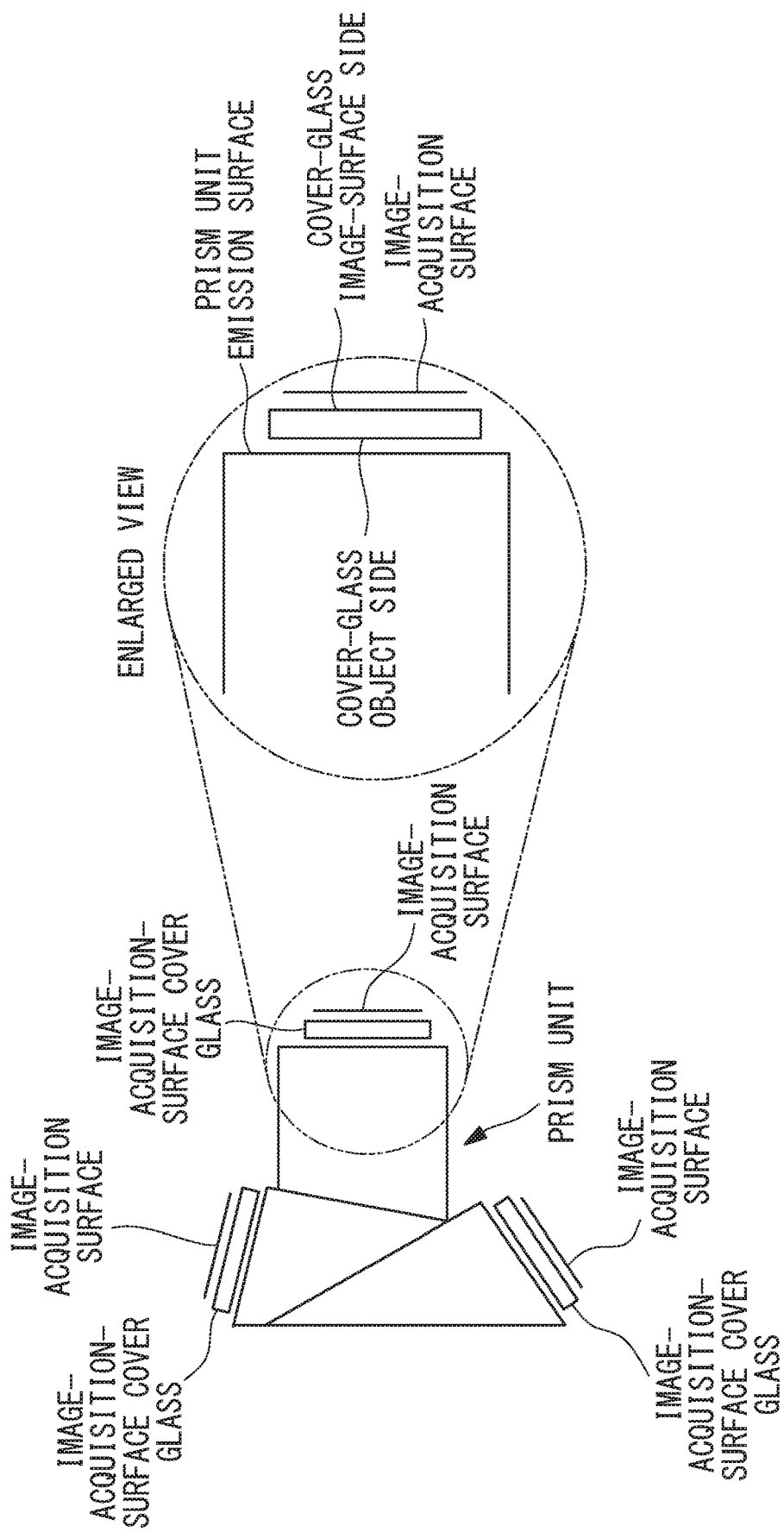
FIG. 25 is a diagram showing a case in which the image-acquisition device in the endoscope in FIG. 21 is a multi-plane image-acquisition device and includes a prism unit.

In addition, as shown in FIG. 25, in the case in which the image-acquisition device is a multi-plane image-acquisition device and includes a prism unit, it is desirable that an anti-reflection film also be provided on an emission surface of the prism unit. It is desirable that the anti-reflection film be provided on at least one of an object side of the cover glass, an image-surface side thereof, and the emission surface of the prism unit, and providing anti-reflection films on all of these surfaces is more effective for suppressing ghosts.

As a result, the following forms are derived from the above-described embodiments.

An aspect of the present invention is an endoscope light source apparatus including: a first solid-state light source that is configured to emit a first light beam that includes a first wavelength band; a second solid-state light source that is configured to emit a second light beam that includes a second wavelength band in which a wavelength thereof is longer than in the first wavelength band; a third solid-state light source that is configured to emit a third light beam that includes a third wavelength band differing from the first and second wavelength bands and that generates white light by being combined with at least of the first and second light beams; an optical member that is configured to combine the first light beam and the second light beam with the third light beam to generate a combined light; an optical member that is configured to combine the first light beam and the second light beam with the third light beam to generate a combined light; an optical filter that is configured to be provided so as to be insertable into/retractable from an optical path of the combined light, and that selectively allows the light in the first, second, and third wavelength bands to pass therethrough; and a controller that is configured to control turning on/off of the first, second, and third solid-state light sources, and insertion/retraction of the optical filter, wherein in a white-light illumination mode, the controller causes the optical filter to be retracted from the optical path, and turns on the first, second, and third solid-state light sources, in a first excitation-light illumination mode, the controller causes the optical filter to be inserted into the optical path, turns on the first and second solid-state light sources, and turns on the third solid-state light source so that an intensity of the third light beam becomes lower than intensities of the first light beam and the second light beam, and, in a second excitation-light illumination mode, the controller causes the optical filter to be inserted into the optical path, turns on the first solid-state light source, turns off the second solid-state light source, and turns on the third solid-state light source so that the intensity of the third light beam becomes lower than the intensity of the first light beam.

With this aspect, by controlling the three solid-state light sources and the optical filter with the controller, it is possible to realize the white-light-observation illumination mode and the two types of illumination modes for performing fluorescence observation. Specifically, in the white-light illumination mode, by retracting the optical filter from the optical path and by turning on all of the first, second, and third solid-state light sources, the white light is generated from the first, second, and third light beams. In the first excitation-light illumination mode, by inserting the optical filter into the optical path, by turning on the first and second solid-state light sources, and by weakly turning on the third solid-state light source, an excitation light beam formed of the light in the first and second wavelength bands and a reference light beam formed of light in the third wavelength band are generated. In the second excitation-light illumination mode, by inserting the optical filter into the optical path, by turning on the first solid-state light source, by turning off the second solid-state light source, and by weakly turning on the third solid-state light source, an excitation light beam formed only of light in the first wavelength band and the reference light beam formed of the light in the third wavelength band are generated.

In this case, by providing the two solid-state light sources having different wavelength bands as the fluorescence-observation excitation light sources, switching between the first excitation-light illumination mode and the second excitation-light illumination mode is realized just by turning on/off the second solid-state light source. In other words, an optical filter is not necessary in order to switch between the two types of illumination modes for performing fluorescence observation, and it suffices to have an optical filter for switching between the white-light-observation illumination mode and the fluorescence-observation illumination mode. Because an optical filter is considerably larger as compared to a solid-state light source, it is possible to effectively reduce the size of the entire apparatus by suppressing the number of optical filters.

In the above-described aspect, the optical member may include a first optical member that is configured to combine the first light beam and the second light beam, and a second optical member that is configured to combine the combined light of the first and second light beams generated by the first optical member with the third light beam.

In the above-described aspect, the first wavelength band may be from 390 nm to 440 nm, and the second wavelength band may be from 440 nm to 470 nm.

By doing so, it is possible to achieve a configuration that is suitable for performing fluorescence observation in which purple and blue light beams are used as the excitation light (for example, autofluorescence observation).

In the above-described aspect, the first optical member may have a first dichroic mirror surface that allows one of the first light beam and the second light beam to pass therethrough and reflects the other, the first dichroic mirror surface may possess a first cut-off wavelength at which a transmittance on a transmission-optical-path side thereof becomes 50% and the first light beam and the second light beam overlap with each other, and an intensity of the combined light of the first and second light beams at the first cut-off wavelength may be equal to or greater than 10% of a maximum intensity thereof.

By doing so, by ensuring an intensity that is equal to or greater than 10% of the maximum intensity at the first cut-off wavelength at which the intensity of the white light becomes extremely low, it is possible to generate white light without a missing wavelength, and thus, it is possible to perform white-light observation with high color reproducibility.

In the above-described aspect, the second optical member may have a second dichroic mirror surface that allows one of the combined light of the first and second light beams and the third light beam to pass therethrough and reflects the other, the second dichroic mirror surface may possess a second cut-off wavelength at which a transmittance on a transmission-optical-path side thereof becomes 50% and the combined light of the first and second light beams and the third light beam overlap with each other, and an intensity of the combined light of the first, second, and third light beams at the second cut-off wavelength may be equal to or greater than 10% of a maximum intensity thereof.

By doing so, by ensuring an intensity that is equal to or greater than 10% of the maximum intensity at the second cut-off wavelength at which the intensity of the white light becomes extremely low, it is possible to generate white light without a missing wavelength, and thus, it is possible to perform white-light observation with high color reproducibility.

In the above-described aspect, the first optical member may have a first dichroic mirror surface that allows light in the first wavelength band to pass therethrough and reflects light in the second wavelength band, and the first light beam and the first dichroic mirror surface may possess optical characteristics that satisfy conditional expression (1) below, where I1 max is the maximum intensity of the first light beam in the first wavelength band, I1 is the intensity of the first light beam at a wavelength 10 nm or more away from the first wavelength band on a long-wavelength side thereof, and T1 is the transmittance (%) of the first dichroic mirror surface at a wavelength 10 nm or more away from the first wavelength band on a long-wavelength side thereof.

$$(I1/I1\ \mathrm{max}) \times T1 \leq 0.01 \qquad (1)$$

A long-wavelength component included in the first light beam could act as noise when incident on the image-acquisition device together with fluorescence in the fluorescence observation. By satisfying conditional expression (1), because such a long-wavelength component of the first light beam is satisfactorily removed by the first dichroic mirror surface, it is possible to perform high-contrast fluorescence observation.

In the above-described aspect, the second light beam and the optical filter may possess optical characteristics that satisfy conditional expression (2) below, where I2 max is the maximum intensity of the second light beam in the second wavelength band, I2 is the intensity of the second light beam at a wavelength 10 nm or more away from the second wavelength band on a long-wavelength side thereof, and T2 is the transmittance (%) of the optical filter at a wavelength 10 nm or more away from the second wavelength band on a long-wavelength side thereof.

$$(I2/I2\ max) \times T2 \leq 0.01 \qquad (2)$$

A long-wavelength component included in the second light beam could act as noise when incident on the image-acquisition device together with fluorescence in the fluorescence observation. By satisfying conditional expression (2), because such a long-wavelength component of the second light beam is satisfactorily removed by the optical filter, it is possible to perform high-contrast fluorescence observation.

REFERENCE SIGNS LIST 1, 2 endoscope light source apparatus
11 first solid-state light source
12 second solid-state light source
13 third solid-state light source
21 first optical member
22 second optical member
4 optical filter
5 control portion (controller)
10 fluorescence endoscope
L1 first light beam
L2 second light beam
L3 third light beam

The invention claimed is:

1. An endoscope light source apparatus comprising:
a first solid-state light source that is configured to emit a first light beam that includes a first wavelength band;
a second solid-state light source that is configured to emit a second light beam that includes a second wavelength band in which a wavelength thereof is longer than in the first wavelength band;
a third solid-state light source that is configured to emit a third light beam that includes a third wavelength band differing from the first and second wavelength bands and that generates white light by being combined with at least one of the first and second light beams;
an optical member that is configured to combine the first light beam and the second light beam with the third light beam to generate a combined light;
an optical filter that is configured to be provided so as to be insertable into and retractable from an optical path of the combined light, and that selectively allows the light in the first, second, and third wavelength bands to pass therethrough; and
a controller that is configured to control turning on and off of the first, second, and third solid-state light sources, and insertion and retraction of the optical filter,
wherein:
in a white-light illumination mode, the controller causes the optical filter to be retracted from the optical path, and turns on the first, second, and third solid-state light sources,
in a first excitation-light illumination mode, the controller causes the optical filter to be inserted into the optical path, turns on the first and second solid-state light sources, and turns on the third solid-state light source so that an intensity of the third light beam becomes lower than intensities of the first light beam and the second light beam, and
in a second excitation-light illumination mode, the controller causes the optical filter to be inserted into the optical path, turns on the first solid-state light source, turns off the second solid-state light source, and turns on the third solid-state light source so that the intensity of the third light beam becomes lower than the intensity of the first light beam.

2. The endoscope light source apparatus according to claim 1, wherein the optical member comprises:
a first optical member that is configured to combine the first light beam and the second light beam, and
a second optical member that is configured to combine the combined light of the first and second light beams generated by the first optical member with the third light beam.

3. The endoscope light source apparatus according to claim 1, wherein:
the first wavelength band is from 390 nm to 440 nm, and
the second wavelength band is from 440 nm to 470 nm.

4. The endoscope light source apparatus according to claim 2, wherein:
the first optical member has a first dichroic mirror surface that allows one of the first light beam and the second light beam to pass therethrough and reflects the other,
the first dichroic mirror surface possesses a first cut-off wavelength at which a transmittance on a transmission-optical-path side thereof becomes 50% and the first light beam and the second light beam overlap with each other, and
an intensity of the combined light of the first and second light beams at the first cut-off wavelength is equal to or greater than 10% of a maximum intensity thereof.

5. The endoscope light source apparatus according to claim 2, wherein:
the second optical member has a second dichroic mirror surface that allows one of the combined light of the first and second light beams and the third light beam to pass therethrough and reflects the other,
the second dichroic mirror surface possesses a second cut-off wavelength at which a transmittance on a transmission-optical-path side thereof becomes 50% and the combined light of the first and second light beams and the third light beam overlap with each other, and
an intensity of the combined light of the first, second, and third light beams at the second cut-off wavelength is equal to or greater than 10% of a maximum intensity thereof.

6. The endoscope light source apparatus according to claim 2, wherein:
the first optical member has a first dichroic mirror surface that allows light in the first wavelength band to pass therethrough and reflects light in the second wavelength band, and
the first light beam and the first dichroic mirror surface possess optical characteristics that satisfy conditional expression (1) below:

$$(I1/I1\ max) \times T1 \leq 0.01 \qquad (1),$$

where:
I1 max is a maximum intensity of the first light beam in the first wavelength band,
I1 is an intensity of the first light beam at a wavelength 10 nm or more away from the first wavelength band on a long-wavelength side thereof, and
T1 is a transmittance (%) of the first dichroic mirror surface at a wavelength 10 nm or more away from the first wavelength band on a long-wavelength side thereof.

7. The endoscope light source apparatus according to claim 1, wherein:

the second light beam and the optical filter possess optical characteristics that satisfy conditional expression (2) below:

$$(I2/I2\ max) \times T2 \leq 0.01 \qquad (2),$$

where:

I2 max is a maximum intensity of the second light beam in the second wavelength band, I2 is an intensity of the second light beam at a wavelength 10 nm or more away from the second wavelength band on a long-wavelength side thereof, and T2 is a transmittance (%) of the optical filter at a wavelength 10 nm or more away from the second wavelength band on a long-wavelength side thereof.

* * * * *